(12) United States Patent
Li et al.

(10) Patent No.: US 11,406,397 B2
(45) Date of Patent: Aug. 9, 2022

(54) ELECTROSTATIC ATOMIZATION ULTRASONIC AIDED LOW-DAMAGE AND CONTROLLABLE BIOLOGIC BONE GRINDING PROCESS AND DEVICE

(71) Applicant: QINGDAO UNIVERSITY OF TECHNOLOGY, Shandong (CN)

(72) Inventors: Changhe Li, Qingdao (CN); Min Yang, Qingdao (CN); Yanbin Zhang, Qingdao (CN); Dongzhou Jia, Qingdao (CN); Naiqing Zhang, Qingdao (CN); Yali Hou, Qingdao (CN); Xiaowei Zhang, Qingdao (CN)

(73) Assignee: QINGDAO UNIVERSITY OF TECHNOLOGY, Qingdao (CN)

( * ) Notice: Subject to any disclaimer, the term of this patent is extended or adjusted under 35 U.S.C. 154(b) by 982 days.

(21) Appl. No.: 16/090,778

(22) PCT Filed: Feb. 2, 2018

(86) PCT No.: PCT/CN2018/075017
§ 371 (c)(1),
(2) Date: Oct. 2, 2018

(87) PCT Pub. No.: WO2019/100587
PCT Pub. Date: May 31, 2019

(65) Prior Publication Data
US 2019/0150955 A1    May 23, 2019

(30) Foreign Application Priority Data

Nov. 21, 2017 (CN) .......................... 201711164696.1
Nov. 21, 2017 (CN) .......................... 201721568840.3

(51) Int. Cl.
*A61B 17/16* (2006.01)
*A61B 17/32* (2006.01)

(52) U.S. Cl.
CPC ...... *A61B 17/1644* (2013.01); *A61B 17/1615* (2013.01); *A61B 17/1622* (2013.01);
(Continued)

(58) Field of Classification Search
CPC ....................................... A61B 17/16–17/1697
See application file for complete search history.

(56) References Cited

U.S. PATENT DOCUMENTS 3,027,625 A * 4/1962 Milstead .............. B23Q 11/141
                                                              184/26
5,624,393 A    4/1997 Diamond
(Continued)

FOREIGN PATENT DOCUMENTS

CN          2759423 Y       2/2006
CN        101947126 B       9/2012
(Continued)

OTHER PUBLICATIONS

Jul. 5, 2018 International Search Report issued in International Patent Application No. PCT/CN2018/075017.
(Continued)

*Primary Examiner* — Zade Coley
(74) *Attorney, Agent, or Firm* — Oliff PLC

(57) ABSTRACT

An electrostatic atomization ultrasonic aided low-damage and controllable biologic bone grinding process and device, which solve the problem of debris blockage and have good cooling effect and high operation efficiency. The device includes: a spindle, arranged rotatably; a water-catching grinding tool for grinding a biologic bone, the spindle being connected with the tool through an ultrasonic vibration mechanism, the tool achieving longitudinal and rotary motions under the drive of the spindle and mechanism; a cooling and film forming mechanism on one side of the tool and connected with an ultrasonic generator in the mecha-
(Continued)

Figure 1:
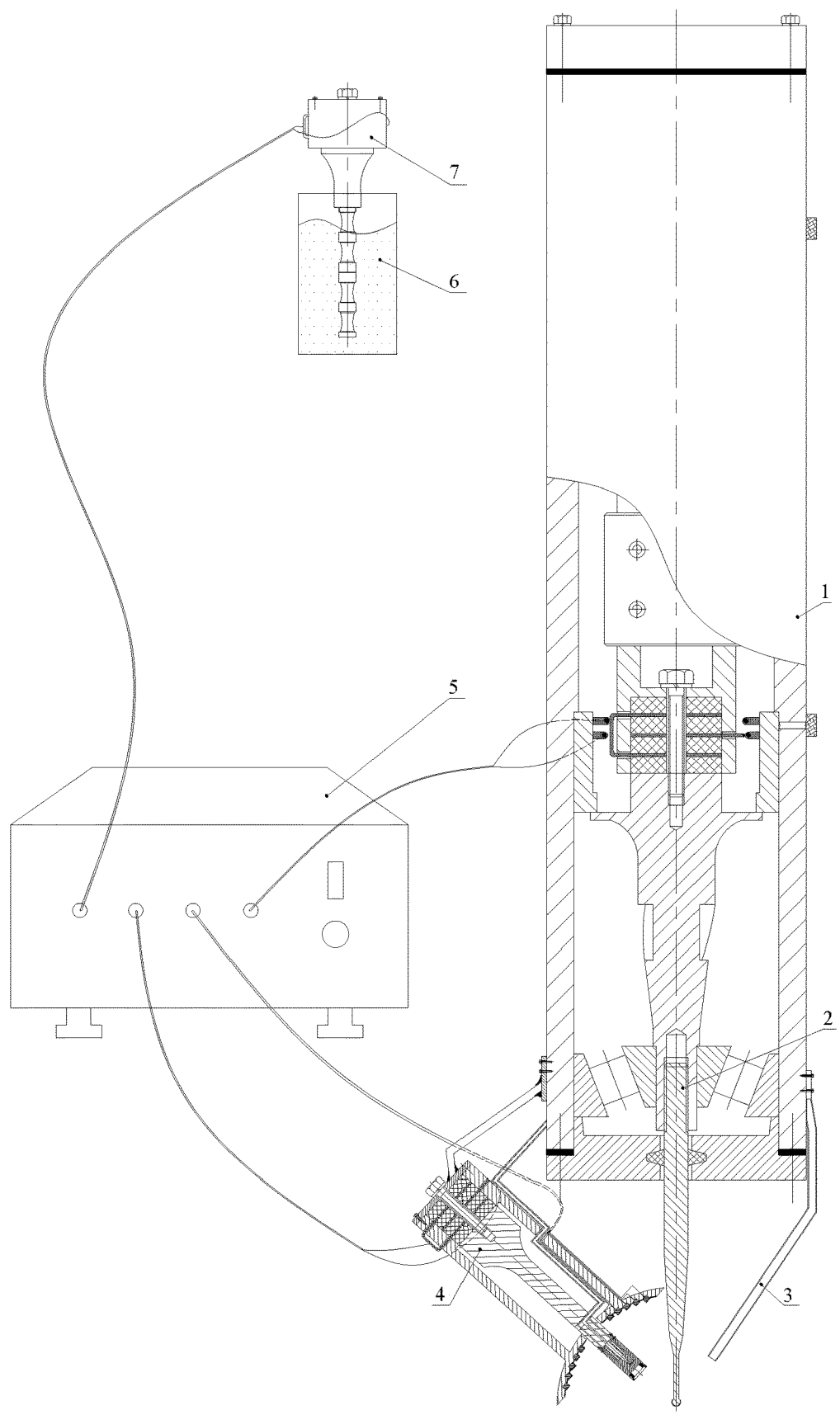

nism, a nozzle connected with a medical nano liquid storage cup arranged at the bottom, compressed gas capable of being introduced into the nozzle to perform pneumatic-ultrasonic atomization on a medical nanofluid, the nanofluid being flushed into a grinding zone in droplets for effective cooling and lubrication; and an endoscope on the other side of the tool.

9 Claims, 11 Drawing Sheets

(52) U.S. Cl.
CPC .. *A61B 17/1633* (2013.01); *A61B 17/320068* (2013.01); *A61B 2017/1651* (2013.01)

(56) References Cited

U.S. PATENT DOCUMENTS

| | | | |
|---|---|---|---|
| 5,651,834 A * | 7/1997 | Jon | B24C 3/12 451/39 |
| 6,443,969 B1 | 9/2002 | Novak et al. | |
| 2010/0011923 A1 * | 1/2010 | Suda | C10M 169/04 451/7 |

FOREIGN PATENT DOCUMENTS

| | | |
|---|---|---|
| CN | 101972159 B | 9/2012 |
| CN | 103054624 B | 11/2014 |
| CN | 103300906 B | 2/2015 |
| CN | 204135897 U | 2/2015 |
| CN | 204971447 U | 1/2016 |
| CN | 205006970 U | 2/2016 |
| CN | 104257428 B | 5/2016 |
| CN | 105997189 A | 10/2016 |
| CN | 104771202 B | 6/2017 |
| CN | 206355101 U | 7/2017 |
| CN | 105147356 B | 9/2017 |
| CN | 107184245 A | 9/2017 |
| CN | 105105819 B | 10/2017 |
| CN | 107789030 A | 3/2018 |
| CN | 107789031 A | 3/2018 |
| WO | 99/33510 A1 | 7/1999 |

OTHER PUBLICATIONS

Min Yang et al. "Research on Microscale Skull Grinding Temperature Field Under Different Cooling Conditions". Applied Thermal Engineering, vol. 126, 2017, pp. 525-537.

* cited by examiner

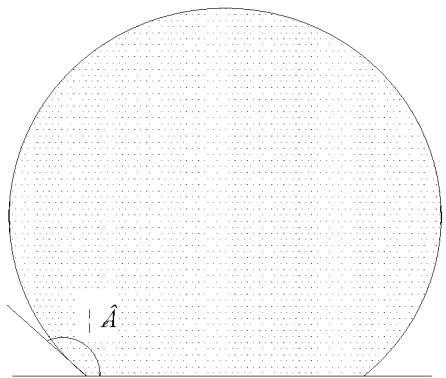
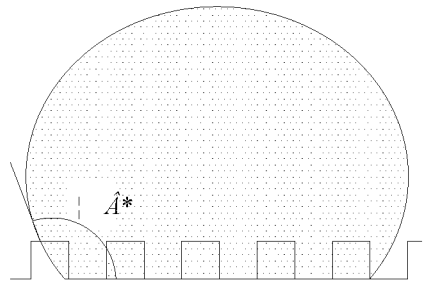
Fig. 9  Fig. 10
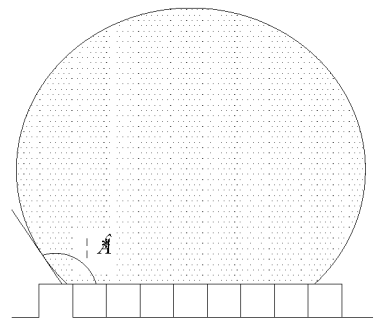
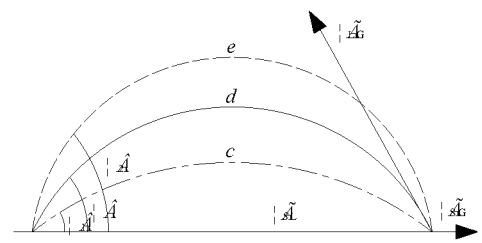
Fig. 11  Fig. 12
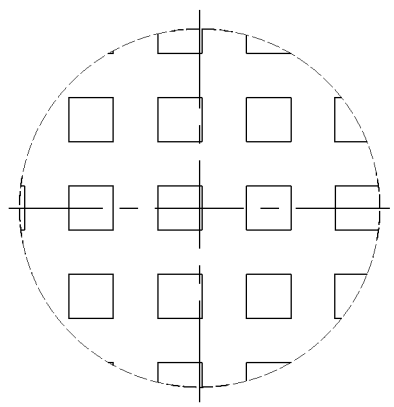
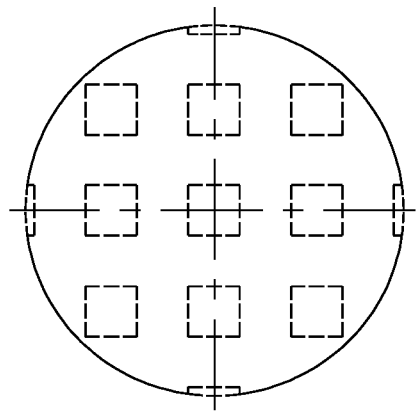
Fig. 13  Fig. 14

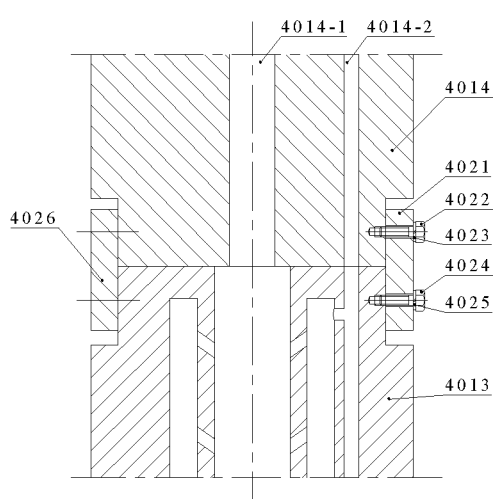
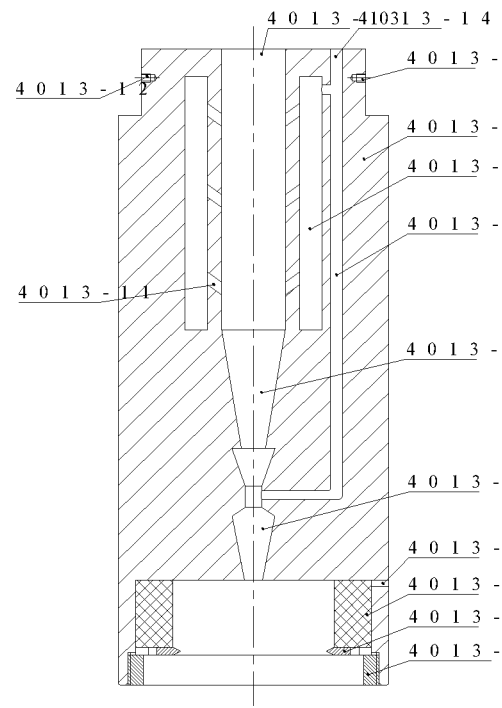
Fig. 19
Fig. 20

ELECTROSTATIC ATOMIZATION ULTRASONIC AIDED LOW-DAMAGE AND CONTROLLABLE BIOLOGIC BONE GRINDING PROCESS AND DEVICE

FIELD OF THE INVENTION

The present invention relates to a flexible integrated device for neurosurgical skull grinding, intraoperative cooling and postoperative wound film forming, particularly to an electrostatic atomization ultrasonic aided low-damage and controllable biologic bone grinding device.

BACKGROUND OF THE INVENTION

In the process of skull base tumor removal surgery, using pituitary tumors as an example, a surgeon first removes nasal septum, anterior sphenoid sinus bone, sella turcica on the posterior sphenoid sinus and other bone structures using a high-speed grinding tool. As the structure of the skull base is complicated and important nerves (e.g., optic nerve, trigeminal nerve, carotid artery) are distributed thereon, the surgeon also needs to remove the bone structures surrounding these nerves to identify the locations of these nerves and protect them. Diamond grinding tools are favored by neurosurgeons because they cause small trauma to soft tissues. However, the heat produced by the diamond grinding tools during grinding is significantly higher than that of other cutting methods, resulting in osteonecrosis and thermal damage to surrounding tissues, and also affecting the coagulation function of tissues to a certain extent. Bone grinding is a common operation in the process of skull base tumor removal surgery. Because there is still no breakthrough in the key technology of accurate control on the grinding temperature field of anisotropic, hard and brittle materials, high-temperature thermal damage is a technical bottleneck of neurosurgical skull grinding at present. However, the current basic research on bone grinding heat is very limited. Yang et al. researched microscale bone grinding surface temperatures under dry, dripping, mist and nanoparticle jet mist cooling conditions and arrived at the conclusion that nanoparticle jet mist cooling has an ideal cooling effect, and researched the influence rule of different nanoparticles on the bone grinding temperature under the nanoparticle jet mist cooling condition by adding hydroxyapatite, $SiO_2$, $Fe_2O_3$ nanoparticles and carbon nanotubes to normal saline. The results show that the nanoparticles have different thermophysical properties and also have different influence on the surface temperature of the bone [Yang M., Li C. H., Zhang Y. B., et al. Research on microscale skull grinding temperature field under different cooling conditions. Applied Thermal Engineering, 2017, Vol 126 pp. 525-537].

In view of the current bottleneck of high-temperature thermal damage in clinical skull grinding, Professor Li Changhe from Qingdao University of Technology researched bone grinding equipment. Upon retrieval, the result showed that Zhang Dongkun et al. invented a medical surgical six-degree-of-freedom automatic adjusting manipulator grinding and clamping device (patent number: ZL 201310277636.6), which has totally six degrees of freedom including three for rotation and three for movement and can be used for implementing the skull surgery operation of any pose. The device is mainly operated by means of advanced surgical instruments, and has obvious advantages in terms of treatment effect, pain relief, recovery period, medical cost and the like by using a six-degree-of-freedom automatic adjusting manipulator and a clamping device mounted at the front end of the manipulator;

Zhang Dongkun et al. invented a surgical skull grinding temperature online detection and controllable handheld grinding device (patent number: ZL 201310030327.9), in which the rotation speed of a grinding wheel is adjusted by monitoring acoustic emission signals of bone grinding to reduce the grinding temperature during the bone grinding process, thereby effectively avoiding thermal damage to brain tissues. An acoustic emission sensor is arranged at the junction of the grinding wheel and a casing, the acoustic emission signals during bone grinding detected by the acoustic emission sensor are received by a signal analysis processing module to determine whether overheat occurs, and the rotation speed of a DC motor is controlled by a feedback device;

Yang Min et al. invented a multi-degree-of-freedom skull surgery grinding experimental platform (patent number: ZL 201410510448.8), including a minimum quantity lubrication system, a three-degree-of-freedom platform, an electric spindle rotating device, an electric spindle, a grinding force measuring device and a grinding temperature measuring device. The grinding temperature is accurately measured using three thermocouples in stepped distribution, the grinding force is measured using a grinding dynamometer, and guidance is provided for clinical practice by analyzing experimental data;

Yang Min et al. invented a handheld surgical grinding temperature online detection and nanofluid phase change heat transfer grinding device (patent number: ZL 201510218166.5), in which the grinding head is a nanofluid phase change heat transfer grinding head, and the heat produced in a grinding zone is taken away by continuous evaporation, condensation and backflow of a nanofluid to reduce the temperature and reduce the secondary damage to a patient; the circumference of abrasive particles is coated with fluorescent powder that is safe for human body, a fluorescence afterglow decay time constant is detected by a fiber sensor, and the temperature to be measured is detected using the dependence of fluorescence on the temperature to realize losed-loop control on the temperature during the grinding process; a reflective strip is adhered to a driven shaft, and the fiber sensor detects the rotation speed and torque of the grinding head on line by adopting the principle of phase comparison measurement and using a laser head and the reflective strip as signal generators, thereby realizing closed-loop control on the pathological bone removal and the service life of the grinding head;

Yang Min et al. invented an orthopedic surgery grinding experimental device integrating cooling and electrostatic atomization film formation (patent number: ZL 201510604889.9), in which an electrostatic atomization inner cooling grinding tool and an electrostatic atomization film forming device form a sleeve structure, which enables full atomization of a coolant and controllable distribution of coolant droplets, thereby effectively reducing the temperature of a grinding zone; medical dressings can be timely sprayed to a ground wound surface through the electrostatic atomization film forming device during bone grinding; the position of an electrostatic atomization film forming nozzle is adjusted by adjusting the telescopic sleeve structure to realize atomization film forming protection on the ground wound surface;

Yang Min et al. invented an electrostatic atomization inner-cooled grinding head (patent number: ZL 201510604803.2), in which a high voltage conversion device is sleeved on the outer side of a grinding head handle and arranged fixedly, a wire connecting block is movably connected with the high voltage conversion device, and the high voltage conversion device is connected with a power supply. An inner cooling hole is provided in the grinding head handle, the inner cooling hole runs through the grinding head and the grinding head handle, and the wire connecting block is connected with the inner cooling hole through a wire. The inner cooling hole is a double spiral duct. During the grinding process, compressed air, a coolant or a nanofluid is accelerated through two spiral holes and then directly sprayed to a grinding zone, thereby effectively reducing the temperature of the grinding zone, washing away abrasive dust and prolonging the service life of a tool.

Luan Nan et al. from Shanghai Jiaotong University invented an orthopedic auxiliary robot system (patent number: ZL 201010299237.6) in the technical field of medical devices, including a robot body, a controller and a joystick, wherein the joystick is located at the wrist of the robot body and connected with the robot controller to transmit a manual operation signal of an operator, and is manipulated by a chief surgeon to adjust the working position of the robot; the controller is located in a base of the robot body and connected with the robot body and the joystick, and can realize autonomous control on the robot body; the robot body is placed beside an operating table to assist the chief surgeon to accomplish the operations of osteotomy, grinding, fixation and the like.

Du Zhijiang et al. from Harbin Institute of Technology invented a six-degree-of-freedom cervical vertebrae grinding parallel robot (patent number: ZL 201010557067.7), in which a grinding drill motor is penetrated through a moving platform, the grinding drill motor is fixedly connected with a grinding drill motor connector, the grinding drill motor connector is fixedly connected with the moving platform, a grinding drill body is fixed on the grinding drill motor connector, the grinding drill body is provided with a grinding drill jack screw hole, a grinding drill jack screw hole cover is installed on the grinding drill jack screw hole of the grinding drill body, a grinding drill shaft is connected with the grinding drill motor through a coupling, and a cutting head is connected with the grinding drill shaft through a tightening nut, thereby solving the problems of insufficient precision, excessive radiation and high working intensity of a surgeon in the existing artificial cervical disc replacement operation.

Tan Yafei et al. from Chongqing Maidefeikuai Science & Technology Co., Ltd. disclosed a grinding drill for bone grinding (application number: 201610407670 .4), including a grinding head and a grinding handle connected with the grinding head, wherein the grinding head is penetrated through a support rod by means of the grinding tool handle, the central axis of the support rod is parallel to the axis of a shank, a limiting device is arranged on the support rod, and the position of the limiting device on the support rod is axially moved and locked under the action of force. The range of resection can be controlled by moving the support rod. The grinding drill is convenient to use and high in resection efficiency, improves the precision and progress of the operation, and is high in controllability, thereby improving the safety of use.

Zhang Lihui et al. from Zhejiang University of Technology disclosed a bone grinding device (application number: 201710436744.1), in which a gas-liquid ratio controllable low-temperature normal saline spray generating device is designed, the spray temperature of normal saline is 0-5° C., and a bone grinding cooling method using less coolant and having high heat exchange efficiency is realized; at the same time, one end of a nozzle is close to a grinding head, and the normal saline is brought into a bone grinding zone by means of a grinding tangential force to ensure that the grinding head can be effectively cooled when moving in different directions.

Upon retrieval, the result showed that all the existing bone grinding devices did not consider the problem of bone debris discharge, so that the grinding tools were severely blocked; the grinding tools were weak in hydrophilicity, and the normal saline cannot be effectively injected into the grinding zone for cooling; the atomization property of the coolant was not considered, and the droplet size of the coolant is large, which is not conducive to spreading of droplets in the grinding zone; the postoperative film forming device is thick in fiber jet and poor in permeability, which is not conducive to filtering bacteria and dust in the air; the grinding devices need to be used together with other equipment, which brings unnecessary additional damage to patients; and the grinding devices have the characteristics of large size, large working space for the surgical devices, high operation difficulty and low operation efficiency.

SUMMARY OF THE INVENTION

In order to overcome the drawbacks of the prior art, the present invention provides an electrostatic atomization ultrasonic aided low-damage and controllable biologic bone grinding device, which realizes longitudinal-torsional and rotary motions of a grinding tool, facilitates timely discharge of bone debris to improve the grinding efficiency and promote the heat discharge with the bone debris, and can realize atomized film forming protection on a ground wound surface.

A specific solution of an electrostatic atomization ultrasonic aided low-damage and controllable biologic bone grinding device is as follows:

An electrostatic atomization ultrasonic aided low-damage and controllable biologic bone grinding device, including:
a spindle, arranged rotatably;
a water-catching grinding tool for grinding a biologic bone, the spindle being connected with the water-catching grinding tool through an ultrasonic vibration mechanism, and the water-catching grinding tool achieving longitudinal and rotary motions under the drive of the spindle and the ultrasonic vibration mechanism;
a cooling and film forming mechanism, arranged on one side of the water-catching grinding tool and connected with an ultrasonic generator in the ultrasonic vibration mechanism, a nozzle connected with a medical nanofluid (a mixture of normal saline and solid nanoparticles) storage cup being arranged at the bottom, compressed gas capable of being introduced into the nozzle to perform pneumatic-ultrasonic atomization on a medical nanofluid, and then the nanofluid being flushed into a grinding zone in the form of droplets for effective cooling and lubrication; at the same time, a postoperative wound being coated; and
an endoscope, arranged on the other side of the water-catching grinding tool.

The above device can realize removal of skull base tumor through the water-catching grinding tool under the endoscope, and jets medical nanofluid during operation through the cooling and film forming mechanism for cooling. The whole device has high integration degree and high grinding efficiency, timely discharges bone debris to ensure the definition of an endoscope lens and shorten the operation time, and achieves low grinding temperature, that is, low-damage and controllable grinding of a biologic bone can be realized using one device.

Further, the cooling and film forming mechanism includes a transducer housing, a horn II is arranged in the transducer housing, four piezoelectric ceramic plates II are arranged at the top of the horn II, and an electrode plate connected with the ultrasonic generator is arranged between two adjacent piezoelectric ceramic plates II, wherein two of the electrode plates share the same electric excitation signal line, and the other electrode plate is connected with the ultrasonic generator from the other side through an electric excitation signal line, so that high-frequency electric oscillation signals are converted into an axial high-frequency vibration; and the horn II is closely connected with the piezoelectric ceramic plate II to amplify the amplitude.

Further, a liquid inlet passage and an air inlet passage are arranged in the horn II, the liquid inlet passage communicates with a nanofluid inlet of the nozzle, and the air inlet passage communicates with a compressed gas inlet of the nozzle; the transducer housing is provided with an opening, a liquid inlet pipe penetrates is connected with the liquid inlet passage through the opening, an air inlet pipe also penetrates through the opening and is connected with the compressed gas inlet, the horn II is inclined relative to the water-catching grinding tool, and the endoscope is also slanted relative to the water-catching tool.

Or a nanofluid passage (communicating with the nanofluid inlet) and a compressed gas passage (communicating with the compressed gas inlet) are provided in the nozzle, an internal compressed gas passage communicating with the nanofluid passage is also provided in the nozzle, an acceleration chamber is arranged at the bottom of the nanofluid passage, the compressed gas passage communicates with the acceleration chamber, and the internal compressed gas passage enters the nanofluid passage through a swirling compressed gas passage;

or the acceleration chamber includes two reducing sections communicating with each other, the first reducing section and the second reducing section are both in the shape of a reverse circular truncated cone, the second reducing section is connected with a third section through a cylinder section, the third section is a vortex chamber, which includes an expanding section and a reducing section.

Further, an electrode supported by an electrode tray is arranged inside the nozzle, the electrode is connected with an external high-voltage electrostatic generator to charge medical nanofluid droplets at the nozzle so as to further refine the nanofluid and obtain superfine fibers for coating the postoperative wound to prevent wound infection; a high-voltage wire is connected with the electrode through the opening of the transducer housing, such that compressed gas enters the nanofluid passage at a set speed through the swirling compressed gas passage and then is mixed with the nanofluid to form a three-phase flow of high-pressure gas, normal saline and solid nanoparticles, the three-phase flow is accelerated in the first and second sections of the acceleration chamber, then enters the vortex chamber to form a vortex with compressed air therein, and the three-phase flow is further mixed and then ejected through the outlet of the nozzle to form droplets. The ejected droplets pass through a drift region of corona discharge of needle electrodes, collide with drifting electrons so as to be charged, and the charged droplets are sprayed controllably to the surface of an action zone under the action of electric field force, pneumatic force and gravity.

Further, the bottom of the transducer housing is of a hemispherical structure, and the bottom of the horn II protrudes from the hemispherical structure of the transducer; a plurality of wafer piezoelectric elements connected with the ultrasonic generator are arranged inside the hemispherical structure, a copper mesh common electrode is arranged on the surface of the wafer piezoelectric elements, and the electric excitation signal line is connected with wafer piezoelectric elements;

or the wafer piezoelectric elements are arranged, in the form of a plurality of concentric circles, on the circumferences of the concentric circles, thus forming an adjustable focus and ensuring efficient injection of the nanofluid droplets into the grinding zone.

Further, the water-catching grinding tool includes a grinding tool handle, a spherical grinding head base is arranged at the bottom of the grinding tool handle, a plurality of square columnar micro-bulges are arranged on the surface of the grinding head base, a nano separator film is adhered between the micro-bulges on the surface of the grinding head base, the micro-bulges enable the nanofluid droplets to be more hydrophilic, the micro-bulges having a feature size of micron scale also serve as abrasive grains for cutting a bone material while adhering the nanofluid droplets, and the edges of the square columns are cutting edges. Further, an ultrasonic vibration bar is arranged in the liquid storage cup and connected with the ultrasonic generator, ultrasonic vibration is performed on the medical nanofluid in the liquid storage cup through the ultrasonic vibration bar, wherein a horn III is arranged at the top of the ultrasonic vibration bar, four piezoelectric ceramic plates III are arranged at the top of the horn III, an electrode plate connected with the ultrasonic generator is arranged between two adjacent piezoelectric ceramic plates III, and a top cover II, the piezoelectric ceramic plates III and the horn III are connected by screws.

Further, the spindle is arranged in an electric spindle housing, a rotor winding is arranged on the circumference of the outer surface of the spindle, and a stator winding corresponding to the rotor winding is arranged in the electric spindle housing; a top cover I is arranged at the top of the transducer housing, a bolt penetrates through the top cover I and the piezoelectric ceramic plates II and is connected with the spindle, and the top cover I is connected with the electric spindle housing through a connecting rod or a connecting plate; and the endoscope body is bent and fixedly connected with the electric spindle housing.

Or the ultrasonic vibration mechanism includes four piezoelectric ceramic plates I, an electrode plate connected with the ultrasonic generator is arranged between two adjacent piezoelectric ceramic plates I, and the bottom piezoelectric ceramic plate I is connected with the top of the water-catching grinding tool through a horn I.

An end cover is respectively arranged at the top and bottom of the electric spindle housing, the water-catching grinding tool penetrates through the bottom end cover, and spiral grooves are arranged on the surface of the horn I to realize longitudinal torsional resonance of the grinding tool.

Or a fiber channel II is arranged inside the electric spindle housing, and a fiber channel I communicating with the fiber channel II is arranged inside the endoscope body.

Further, the spindle is connected with a connecting cylinder through a coupling, the piezoelectric ceramic plates I are arranged at the bottom of the connecting cylinder, a sleeve is arranged inside the electric spindle housing, and electric brushes connected with respective electrode plates are arranged in the sleeve.

In order to overcome the drawbacks of the prior art, the present invention also provides an aided low-damage and controllable biologic bone grinding process using the above-mentioned electrostatic atomization ultrasonic aided low-damage and controllable biologic bone grinding device.

Compared with the prior art, the present invention has the following beneficial effects:

1) Ultrasonic vibration of liquid in the liquid storage cup can be realized through the ultrasonic vibration bar, thereby effectively reducing the viscosity of an electrospinning solution and a melt, expanding the electrospinning concentration range of the device, but also effectively reducing the diameters of fibers, reducing the structural defects of the fibers, thus improving the mechanical properties of the spinning fibers, and ensuring that the spinning system for wound dressing is sprayed onto the postoperative wound surface in the form of spinning fibers after three-level atomization to achieve atomized film forming protection on the ground wound surface.

2) The nozzle is connected with the nanofluid and the compressed gas to realize aerodynamics of the medical nanofluid coolant, the electrodes setting can implement electrostatic treatment on droplets, and the horns can cavitate the droplets, so that the medical nanofluid at the working surface forms superfine droplets after aerodynamic-ultrasonic-electrostatic three-level atomization; and the nanofluid droplets are injected into the grinding tool/bone wedge-shaped constraint space by ultrasonic focusing to effectively cool and lubricate the grinding zone.

3) The longitudinal-torsional and rotary motions of the water-catching grinding tool is achieved by the spindle, which is beneficial to timely discharge of the bone debris and achieves high grinding efficiency.

BRIEF DESCRIPTION OF THE DRAWINGS

The accompanying drawings constituting a part of the present application are used for further understanding of the present application, and the schematic embodiments of the present application and the description thereof are used for interpreting the present application, rather than improperly limiting the present application.

FIG. 1 is an assembly diagram of an electrostatic atomization ultrasonic aided low-damage and controllable biologic bone grinding process and device;

FIG. 2 is a cross-sectional view of a longitudinal torsional resonant rotary ultrasonic electric spindle;

FIG. 3 is a schematic diagram of part of an ultrasonic mechanism;

FIG. 4 shows an exponential segment function of a horn;

FIGS. 5(*a*) and 5(*b*) are force analysis diagrams of a rectangular spiral groove horn;

FIGS. 6(*a*) and 6(*b*) show a triangular fence group through groove horn;

FIG. 7 shows a neurosurgical skull grinding water-catching grinding tool;

FIG. 8 is an enlarged view of the upper part of a grinding tool handle;

FIG. 9 shows a droplet Young's wetting model;

FIG. 10 shows a droplet Wenzel wetting model;

FIG. 11 shows a droplet Cassie wetting model;

FIG. 12 is a schematic diagram of a droplet pinning effect;

FIG. 13 shows a three-phase contact boundary of the Wenzel wetting model;

FIG. 14 shows a three-phase contact boundary of the Cassie wetting model;

FIG. 15 is a surface dimension diagram of square columnar bulge microstructures;

FIG. 16 shows a grinding head base of the water-catching grinding tool and a cross-sectional view;

FIG. 17 is a cross-sectional front view of the grinding head;

FIG. 18 is a cross-sectional view of a three-level atomization focus adjustable ultrasonic focusing nozzle;

FIG. 19 is a connection diagram of a nozzle body and a horn;

FIG. 20 is a cross-sectional view of a pneumatic-electrostatic atomizing nozzle;

FIG. 21 is an assembly diagram of a spherical crown portion of a spherical crown transducer housing and a bottom view thereof;

FIG. 22 is a principle diagram of a focus adjustable transducer;

FIG. 23 is a principle diagram of electrospinning;

FIG. 24 is a diagram showing a liquid path and gas path system of a cooling and film forming mechanism;

FIG. 25 is a connection diagram of the cooling and film forming mechanism and an electric spindle;

FIG. 26 is a half cross-sectional view of an ultrasonic vibration bar;

FIG. 27 is an installation diagram of an endoscope in an electric spindle housing;

FIG. 28 is a cross-sectional view of the interior of the endoscope body.

REFERENCE SIGNS

1—longitudinal torsional resonant rotary electric spindle, 2—water-catching grinding tool, 3—endoscope, 4—cooling and film forming mechanism, 5—ultrasonic generator, 6—liquid storage cup, 7—ultrasonic vibration bar;

101—end cover I, 102—spacer I, 103—electric spindle housing, 104—spindle, 105—power interface I, 106—power line I, 107—stator winding, 108—rotor winding, 109—coupling, 1010—threaded hole I, 1011—connecting cylinder, 1012—short brush, 1013—power interface II, 1014—power line II, 1015—electrode plate I, 1016—sleeve, 1017—horn I, 1018—conical roller bearing I, 1019—threaded hole II, 1020—threaded hole III, 1021—spacer II, 1022—end cover II, 1023—sealing ring, 1024—spring washer I, 1025—screw I, 1026—threaded hole IV, 1027—threaded hole V, 1028—piezoelectric ceramic plate I, 1029—electrode plate II, 1030—long brush, 1031—electrode plate III, 1032—spring washer II, 1033—center screw I, 1034—conical roller bearing II, 1035—screw II, 1036—spring washer III;

201—grinding tool handle, 202—grinding head base;

202-1—partial sphere, 202-2—octagonal cylinder, 202-3—square columnar micro-bulge, 202-4—nano separator film;

301—screw III, 302—spring washer IV, 303—endoscope body, 304—screw IV, 305—spring washer V, 306—fibre channel, 307—fibre channel II, 308—cold light illumination source transmission fiber, 309—endoscopic fiber, 3010—fluorescent excited light transmission fiber, 3011—image transmission fiber;

401—center screw II, 402—spring washer VI, 403—top cover I, 404—spherical crown transducer housing, 405—electric excitation signal line I, 406—electrode plate IV, 407—liquid inlet pipe, 408—air inlet pipe, 409—high voltage wire, 4010—electric excitation signal line II, 4011—plane wafer piezoelectric element, 4012—copper mesh common electrode, 4013—electrostatic atomizing nozzle, 4014—horn II, 4015—piezoelectric ceramic plate II, 4016—electrode plate V, 4017—electric excitation signal line III, 4018—electrode plate VI, 4019—screw V, 4020—spring washer VII, 4021—connecting plate I, 4022—screw VI, 4023—spring washer VIII, 4024—screw VII, 4025—spring washer IX, 4026—connecting plate II, 4027—high-voltage electrostatic generator, 4028—injection pump, 4029—spinning medium, 4030—metal electrode, 4031—fiber jet, 4032—receiving plate; 4033—screw VIII, 4034—spring washer X, 4035—screw IX, 4036—spring washer XI, 4037—connecting plate III, 4038—connecting rod;

4013-1—threaded hole VI, 4013-2—nozzle body, 4013-3—internal compressed gas passage, 4013-4—compressed gas passage, 4013-5—three-phase flow acceleration chamber, 4013-6—vortex chamber, 4013-7—high voltage inlet hole, 4013-8—electrode tray, 4013-9—needle electrode, 4013-10—positioning threaded ring, 4013-11—swirling compressed gas passage, 4013-12—threaded hole VII, 4013-13—nanofluid inlet, 4013-14—compressed gas inlet;

4014-1—liquid inlet passage, 4014-2—air inlet passage;

601—air compressor, 602—filter, 603—gas tank, 604—pressure gauge, 605—pressure regulating valve I, 606—throttle valve I, 607—turbine flow meter I, 608—liquid storage cup I, 609—hydraulic pump I, 6010—reversing valve I, 6011—pressure regulating valve II, 6012—liquid storage cup II, 6013—hydraulic pump II, 6014—reversing valve II, 6015—pressure regulating valve III, 6016—throttle valve II, 6017—turbine flow meter II, 6018—recovery tank, 6019—overflow valve;

701—screw X, 702—spring washer XII, 703—top cover II, 704—transducer housing, 705—electric excitation signal line IV, 706—electrode plate VII, 707—horn III, 708—vibration bar, 709—piezoelectric ceramic plate III, 7010—electrode plate VIII, 7011—electric excitation signal line V, 7012—electrode plate IX, 7013—spring washer XIII, 7014—center screw III.

DETAILED DESCRIPTION OF THE EMBODIMENTS

It should be pointed out that the following detailed description is exemplary and intended to further illustrate the present application. Unless otherwise specified, all technical and scientific terms used herein have the same meanings as generally understood by those of ordinary skill in the art of the present application.

It should be noted that the terms used herein are merely for describing specific embodiments, and are not intended to limit exemplary embodiments according to the present application. As used herein, unless otherwise explicitly pointed out by the context, the singular form is also intended to include the plural form, in addition, it should also be understood that when the terms "include" and/or "comprise" are used in the specification, they indicate the presence of features, steps, operations, devices, components and/or their combinations.

As described in the background, the prior art has drawbacks, so in order to solve the above technical problems, the present application proposes an electrostatic atomization ultrasonic aided low-damage and controllable biologic bone grinding device.

In a typical embodiment of the present application, FIG. 1 shows an assembly diagram of an electrostatic atomization ultrasonic aided low-damage and controllable biologic bone grinding device, including a longitudinal torsional resonant rotary ultrasonic electric spindle 1, a water-catching grinding tool 2, an endoscope 3, a focus adjustable ultrasonic focusing aided three-level atomization cooling and film forming mechanism 4, an ultrasonic generator 5, a liquid storage cup 6 and an ultrasonic vibration bar 7. The longitudinal torsional resonant rotary ultrasonic electric spindle 1 can realize longitudinal-torsional and rotary motions of horns, and the water-catching grinding tool 2 installed can remove pathological bone tissues safely and efficiently with the aid of the endoscope 3; the cooling and film forming mechanism 4 performs pneumatic-ultrasonic-electrostatic three-level atomization on a medical nanofluid, and the nanofluid is finally flushed to a grinding zone in the form of droplets under the action of ultrasonic focusing for effective cooling and lubrication; at the same time, the nanofluid coats the postoperative wound to prevent wound infection; the ultrasonic vibration bar 7 can ultrasonically oscillate the medical nanofluid (or medical spinning medium) in the liquid storage cup 6 to prevent agglomeration of nanoparticles (reduce the viscosity of the spinning medium). The longitudinal torsional resonant rotary ultrasonic electric spindle 1, the cooling and film forming mechanism 4 and the ultrasonic vibration bar 7 share one ultrasonic generator 5.

Figure 2:
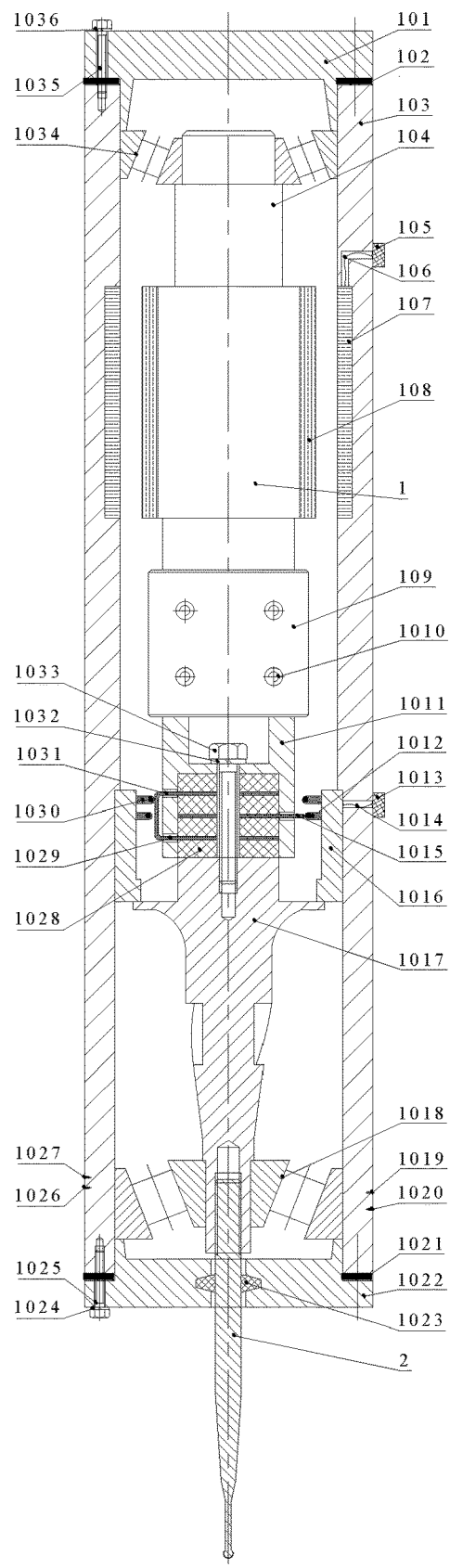

FIG. 2 shows the longitudinal torsional resonant rotary ultrasonic spindle. An end cover I 101 and an end cover II 1022 play a role in axial positioning of bearings, dust proofing and sealing, and are respectively fixed on an electric spindle housing 103 by screws II 1035 and spring washers III 1036 as well as screws I 1025 and spring washers I 1024. Since the grinding device is at an angle with respect to the horizontal direction during actual operation, both a spindle 104 and a horn I 1017 bear axial and radial forces, so a conical roller bearing II 1034 and a conical roller bearing I 1018 are adopted in the device. The conical roller bearing II 1034 is positioned by the end cover I 101 and the shoulder of the spindle 104, and the conical roller bearing I 1018 is positioned by the shoulder of the horn I 1017 and the end cover II 1022. The end cover II 1022 is sealed by a sealing ring 1023 to prevent leakage of lubricating oil, and can also prevent external dust from entering the electric spindle. In addition, the sealing ring 1023 can also reduce friction. A spacer I 102 and a pacer II 1021 can adjust bearing clearances and plays, the spindle 104 thermally expands during rotation, and the thermal elongation of the spindle is adjusted through the spacers. A stator winding 107 is integrated with the electric spindle housing 103. When a power interface I 105 is powered on, the stator winding 107 is energized under the conduction of a power line I 106 to generate a rotating magnetic field, a current flows through a rotor winding 108 and the rotor winding 108 is rotated by the magnetic field. Since the spindle 104 is integrated with the rotor winding 108, the spindle 104 rotates. The spindle 104 is connected with a connecting cylinder 1011 through a coupling 109 and threaded holes I 1010 and rotates, and the connecting cylinder 1011 drives an electrode plate I 1015, an electrode plate II 1029, an electrode plate III 1031, piezoelectric ceramic plates I 1028 and the horn I 1017 to rotate through a center screw I 1033 and a spring washer II 1032.

Figure 3:
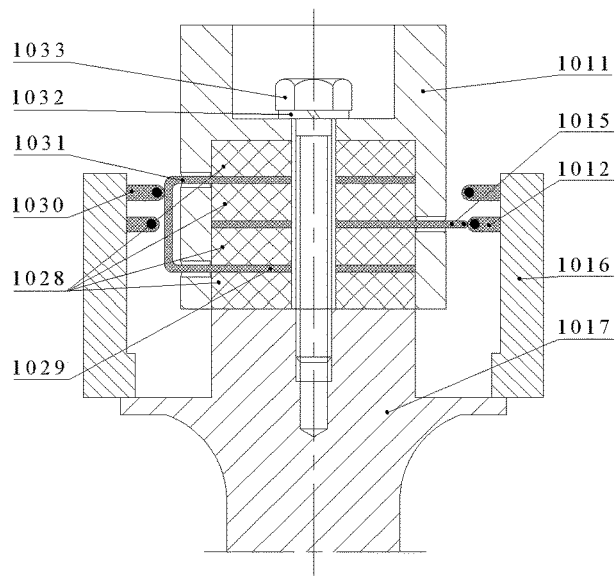

FIG. 3 is a schematic diagram of part of an ultrasonic mechanism. The electrode plate III 1031 and the electrode plate II 1029 are led out from the connecting cylinder 1011 and then connected. During operation, the ultrasonic generator 5 converts alternating current into high-frequency electric oscillation signals, which are respectively transmitted to the electrode plate I 1015, the electrode plate III 1031 and the electrode plate II 1029 by a power interface II 1013 and a power line II 1014 through a short brush 1012 and a long brush 1030 fixed on a sleeve 1016, and the high-frequency electric oscillation signals are converted into an axial high-frequency vibration by the piezoelectric ceramic plates I 1028. However, the amplitude of the vibration is relatively small, and cannot meet the amplitude requirement of skull grinding. Therefore, the lower end of the piezoelectric ceramic plates I 1028 is tightly connected with the horn I 1017, thereby amplifying the amplitude. Finally, the amplified amplitude is transmitted to the grinding tool, causing the grinding tool to generate a vibration that meets the processing requirement.

Figure 4:
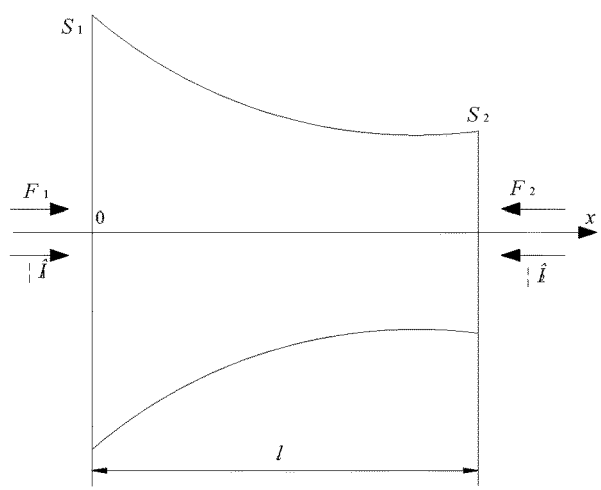

FIG. 4 shows an exponential segment function of the horn. In the case of simple harmonic vibration, the wave equation of propagation of the longitudinal vibration in the variable section horn is:

$$\frac{\partial^2 \xi}{\partial x^2} + \frac{1}{S} \cdot \frac{\partial S}{\partial x} \cdot \frac{\partial \xi}{\partial x} + k^2 \xi = 0 \tag{1}$$

in which: $\xi$ is a displacement function of longitudinal vibration; k is a circular wavenumber, $k=\omega/c$, $\omega$ is an angular frequency, $c=\sqrt{E/\rho}$ is a propagation velocity of longitudinal waves in the horn; and E is a Young's modulus of a material.

As shown in FIG. 4, the horn has a cross-sectional area $S_1$ at the origin (x=0) of coordinates, and has a cross-sectional area $S_2$ at x=l; and the forces and the vibration velocities of longitudinal waves acting on the input end (x=0) and the output end (x=l) of the horn are respectively $F_1$, $\xi_1'$ and $F_2$, $\xi_2'$. The function of the circular cross-sectional radius of the exponential horn is:

$$R = R_1 e^{-\beta x} \tag{2}$$

in which:

$$\beta = \frac{1}{l} \ln \sqrt{\frac{S_1}{S_2}} = \frac{1}{l} \ln \frac{R_1}{R_2} = \frac{1}{l} \ln N,$$

N is an area function, and $$N = \sqrt{\frac{S_1}{S_2}} = \frac{R_1}{R_2}.$$

The solution of equation (1) can be obtained as:

$$\xi = e^{\beta x}(a_1 \cos K'x + a_2 \sin K'x)e^{j\omega t} \tag{3}$$

in which, $K' = \sqrt{K^2 - \beta^2}$.

For the convenience of calculation, a time factor $e^{j\omega t}$ is omitted, and the expression of strain distribution is:

$$\frac{\partial \xi}{\partial x} = \beta e^{\beta x}(a_1 \cos K'x + a_2 \sin K'x)e^{j\omega t} + \tag{4}$$

$$e^{\beta x}(-a_1 K' \sin K'x + a_2 K' \cos K'x)$$

The boundary condition of the horn is free at two ends:

$$x = 0 \; \xi = \xi_1 \; \xi_1' = \begin{cases} \frac{\partial \xi}{\partial t}\Big|_{x=0} & \frac{\partial \xi}{\partial x}\Big|_{x=0} = 0 \\ -\frac{\partial \xi}{\partial t}\Big|_{x=l} & \frac{\partial \xi}{\partial x}\Big|_{x=l} = 0 \end{cases} \tag{5}$$

According to the boundary condition (5) and equations (3) and (4), $a_1 = \xi_1$, and $$a_2 = -\frac{\beta}{K'}\xi_1$$

can be obtained, and substituted into equation (3) to obtain a displacement distribution equation of particles along the axial direction:

$$\xi = \xi_1 e^{\beta x}\left(\cos K'x - \frac{\beta}{K'}\sin K'x\right) \tag{6}$$

According to equation (6), obtained is:

$$\begin{cases} \xi|_{x=0} = \xi_1 \\ \xi|_{x=l} = \xi_1 e^{\beta l}\left(\cos K'l - \frac{\beta}{K'}\sin K'l\right) \\ M_P = \left|\frac{\xi|_{x=l}}{\xi|_{x=0}}\right| = e^{\beta l}\left(\cos K'l - \frac{\beta}{K'}\sin K'l\right) \end{cases} \tag{7}$$

A frequency equation $k'l = n\pi$ is substituted into equation (7) to obtain an amplification factor $M_P$ of the exponential horn:

$$M_P = e^{\beta l} = N \tag{8}$$

Figures 5A, 5B:
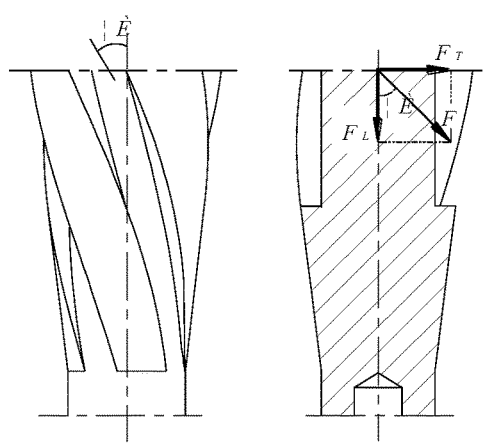

FIG. 5(a) and FIG. 5(b) are force analysis diagrams of rectangular spiral grooves of the horn I 1017. It can be seen from the diagrams that the force can be decomposed into an axial force $F_L$, and a tangential force $F_T$ through the spiral grooves, and the relationship between them is:

$$\begin{cases} F_L = F\cos\theta \\ F_T = F\sin\theta \end{cases} \tag{9}$$

in which: $\theta$ is the inclination angle of the spiral groove.

It can be known from the theory of mechanical vibration that $F_T$ produces a torsional vibration and $F_L$ produces a longitudinal vibration. The torque M at the spiral grooves can be expressed as:

$$M = \int rf\, dS \tag{10}$$

in which: r is the distance from any point on the helical surface to the central axis; f is the tangential stress at any point on the helical surface; dS is a differential at r, and:

$$S = \pi r^2 - \pi(r - r_1)^2, r_1 < r < r_2 \tag{11}$$

in which: $r_1$ is the distance from the bottom of the spiral groove to the central axis; and $r_2$ is the distance from the top of the spiral groove to the central axis. Equation (11) is derived to obtain:

$$dS = 2\pi r_1 dr \tag{12}$$

Equation (12) is substituted into equation (10) to obtain:

$$M = \int_{r_1}^{r_2} r \frac{F\sin\theta}{2\pi r r_1 - \pi r_1^2} 2\pi r_1 dr \tag{13}$$

Equation (13) is integrated to obtain $$M = 2F\sin\theta\left(\frac{r_2}{2} - \frac{r_1}{2} - \frac{r_1}{4}\ln r_1 + \frac{r_1}{4}\ln|2r_2 - r_1|\right) \quad (14)$$

Figures 6A, 6B:
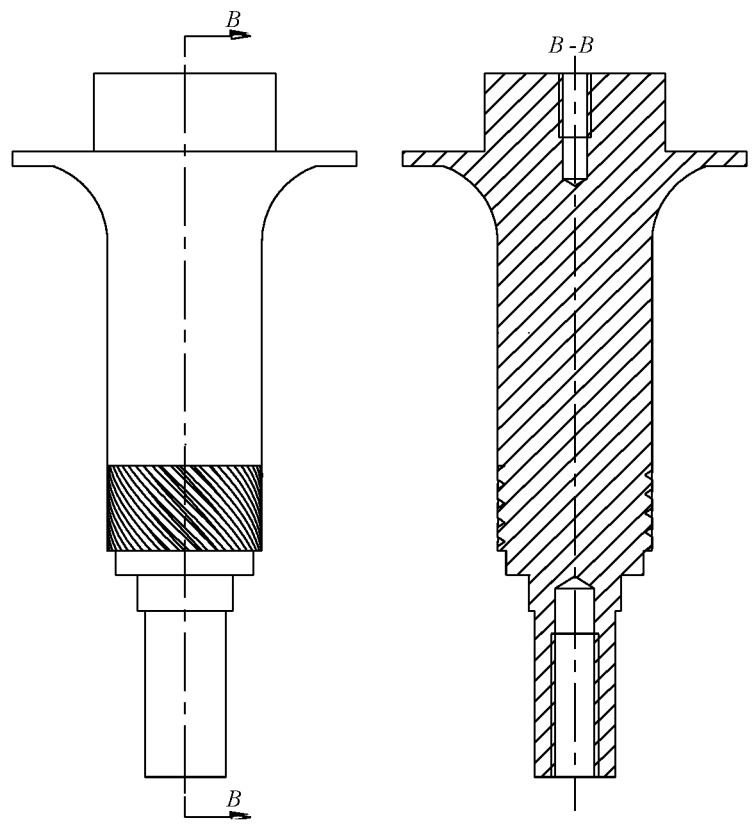

It can be seen from equation (14) that the spiral grooves can produce not only a longitudinal vibration but also a torsional vibration, thereby realizing a longitudinal-torsional composite vibration of the horn. The spiral grooves may be rectangular spiral grooves or arc spiral grooves, or triangular, rectangular or trapezoidal fence group through grooves, which can decompose the longitudinal waves to excite the torsional vibration. FIGS. 6(a) and 6(b) are cross-sectional views of a horn with triangular fence group through grooves. A threaded hole at the upper end of the horn I 1017 is fastened with the center screw I 1033, a threaded hole at the lower end is fastened with the grinding tool handle 201, and the thread directions of the two threaded connections are opposite to the direction of rotation.

Figures 7, 8:
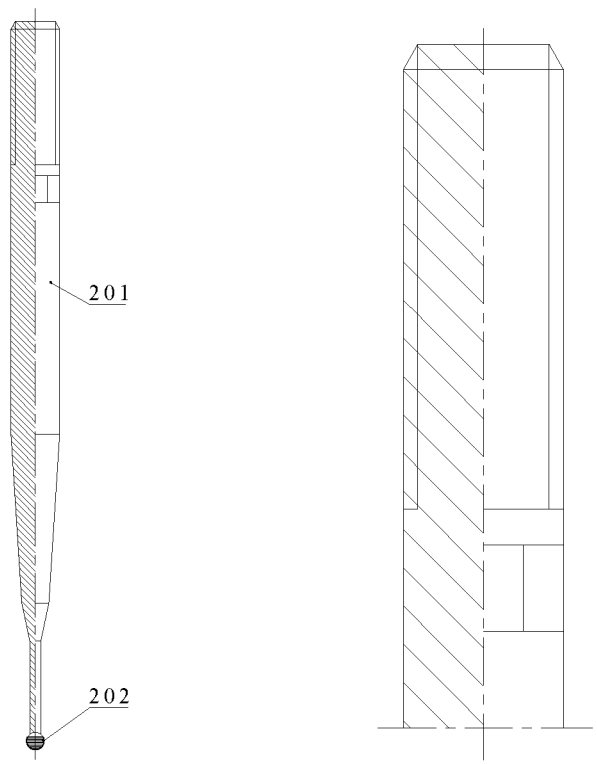

As shown in FIG. 7, the water-catching grinding tool 2 includes a grinding tool handle 201 and a grinding head base 202. FIG. 8 shows the upper part of the grinding tool handle 201. Threads are machined at the upper end of the grinding tool handle 201 and fastened with the threaded hole at the lower end of the horn I 1017.

FIG. 9 shows a wet state of droplets on a smooth flat surface, $\beta_e$ is an intrinsic contact angle of the droplets on the smooth flat surface (Young model), and FIGS. 10 and 11 show a wet state of droplets on a rough surface, respectively Wenzel and Cassie models.

The Wenzel model believes that the actual solid-liquid contact area is greater than the apparent geometric contact area in the presence of a rough surface, which geometrically enhances the hydrophilicity (or hydrophobicity). As shown in FIG. 10, it is assumed that the groove structures on the surface are always full of droplets, the relationship between the apparent contact angle $\beta^*$ of the rough surface and $\beta_e$ is:

$$\cos\beta^* = r(\gamma_{SG} - \gamma_{SL})/\gamma_{LG} = r\cos\beta_e \quad (15)$$

in which: $\gamma_{SG}$, $\gamma_{SL}$ and $\gamma_{LG}$ are respectively surface tensions of solid-gas, solid-liquid, and liquid-gas contact surfaces; r is a surface roughness factor of a material and is the ratio of the actual contact area to the apparent contact area, $r \geq 1$. Therefore, the apparent contact angle can be adjusted by changing the solid surface roughness to change the wettability of the solid surface.

As shown in FIG. 11, in the Cassie model, the contact of droplets on the rough surface is regarded as a composite contact, the grooves in the rough surface cannot be full of the droplets, and trapped air is present under the droplets in the grooves, so that the apparent liquid-solid contact is actually composed of liquid-solid and gas-solid contacts, thermodynamically:

$$dG = f_s(\gamma_{SL} - \gamma_{SG})dx + (1-f_s)\gamma_{LG}dx + \gamma_{LG}dx\cos\beta^* \quad (16)$$

When the droplets are balanced, the apparent contact angle $\beta^*$ of the rough surface is a mean of the intrinsic contact angles $\beta_e$ of the smooth flat surface and 180°:

$$\cos\beta^* = f_s(1+\cos\beta_e) - 1 \quad (17)$$

in which: $f_s$ is an area fraction of raised solids in the composite contact surface ($f_s < 1$). A three-phase contact boundary is the most important factor affecting the dynamic behavior of surface droplets. As shown in FIG. 12, when the droplets are balanced, the contact angle is $\beta$ (state d); when a small amount of liquid is added, the solid-liquid-gas three-phase contact boundary remains stationary, and the contact angle is necessarily increased to $\beta_2$ (state e); conversely, if a small amount of liquid is drawn while the solid-liquid-gas three-phase contact boundary is kept stationary, the contact angle is necessarily reduced to $\beta_1$ (state c). It is assumed that the solid-liquid-gas three-phase contact boundary has only three interfacial tensions. When balanced, states d, e and c satisfy:

$$\cos\beta = \cos\beta_1 = \cos\beta_2 = \frac{\gamma_{SG} - \gamma_{SL}}{\gamma_{LG}} \quad (18)$$

In order for the droplets at the balanced spread position continue to spread along the solid wall, it is necessary to overcome the pinning effect of the solid on the contact boundary. During the cooling process of neurosurgical skull grinding, a coolant continuously flows into the grinding zone. The previous coolant droplet impacts on the surface of the bone at certain speed and angle and is spread into a liquid film. The most favorable status for the cooling and lubrication effect is that the subsequent droplet is continuously spread when impacting on the position of the previous droplet and, i.e., the coolant droplets can overcome the pinning effect of the rough bone surface on the contact boundary. The dashed lines in FIGS. 13 and 14 are solid-liquid-gas three-phase contact boundaries of droplets in Wenzel and Cassie wet states, respectively. It can be seen from the figures that the three-phase contact boundary of droplets in the Wenzel model is long and continuous, while the three-phase contact boundary of droplets in the Cassie model is short and discontinuous. When the three-phase contact boundary is long and continuous, the energy barrier to be crossed by the droplets to continuously spread along the solid wall is low, and the three-phase contact boundary is prone to pinning-de-pinning transformation, so the spreading characteristic is good; when the three-phase contact boundary is short and discontinuous, the droplets are obvious in lag effect and poor in spreading characteristic.

Since the hydrophilicity/hydrophobicity of the surface of human skull to coolant droplets is unknown and uncontrollable, the grinding tool can be designed with microstructures on the surface to have a water-catching property, thereby improving the cooling and lubricating performance of the medical nanofluid droplets. Combining the analysis on the wet state of the coolant droplets and the solid-liquid-gas three-phase contact boundary, it can be seen that after the droplets impact on the microstructure surface of the grinding tool, the droplets can be spread at small contact angles and can overcome the pinning effect of the grinding tool on the contact boundary, i.e., the wet state of the droplets is closer to the Wenzel model, and the microstructure surface is the most favorable surface for cooling and lubrication of skull grinding. A micro-bulge structure is more beneficial than a micro-pit structure to preventing the Wenzel/Cassie wet state transition, and is more suitable for manufacturing the water-catching grinding tool.

Figure 15:
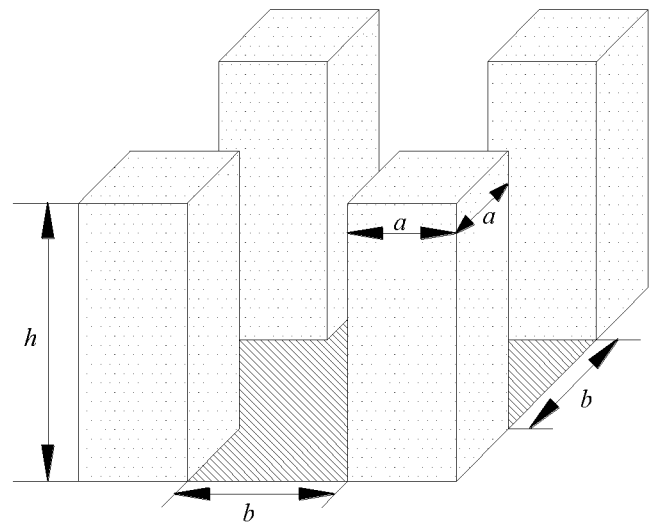

FIG. 15 shows a surface dimension diagram of square columnar bulge microstructures, in which the size of a micro-bulge is a×a, the height is h, the spacing between the micro-bulges is b, the roughness factor r and the area fraction $f_s$ occupied by the protruding solids in the contact surface are:

$$\begin{cases} r = \dfrac{(a+b)^2 + 4ah}{(a+b)^2} \\ f_s = \dfrac{a^2}{(a+b)^2} \end{cases} \quad (19)$$

Two three-dimensional surface characteristic values are introduced: σ=b/a, τ=h/a. Equation (19) is substituted into (15) and (17) to obtain:

$$\cos\beta^* = r\cos\beta_e = \frac{(a+b)^2 + 4ah}{(a+b)^2}\cos\beta_e \quad (20)$$

$$\cos\beta^* = f_s(1+\cos\beta_e) - 1 = \frac{a^2}{(a+b)^2}(1+\cos\beta_e) - 1 = \frac{1+\cos\beta_e}{(1+\beta)^2} - 1 \quad (21)$$

It can be seen from equation (20) that for the Wenzel model, when σ is constant, the hydrophobic material can be more hydrophobic and the hydrophilic material can be more hydrophilic by improving the τ, and when τ is constant, the hydrophobic material can be more hydrophobic and the hydrophilic material can be more hydrophilic by reducing the σ.

Figure 16:
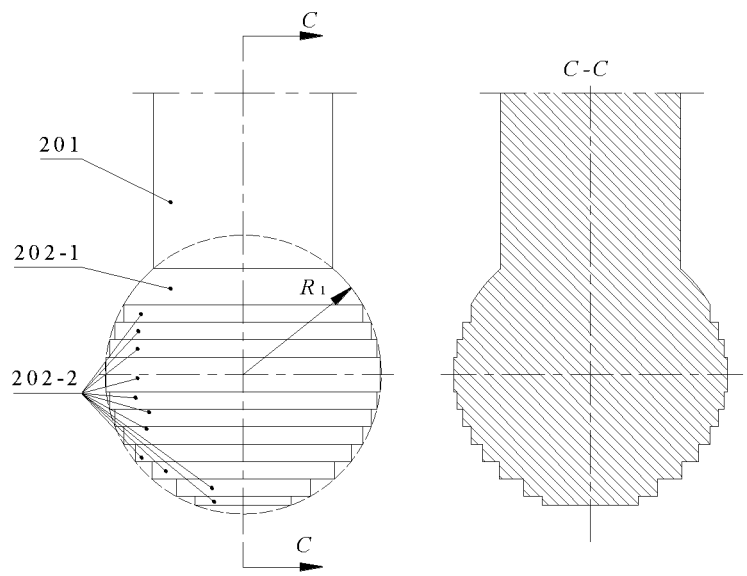

It can be seen from equation (21) that for the Cassie model, when a hydrophobic material has certain $\beta_e$ (>90°), if the hydrophobic property of the material is to be improved (i.e., larger β*), σ should be larger; when the hydrophilic material has certain $\beta_e$ (<90°), if the hydrophilic property of the material is to be improved (i.e., smaller β*), σ should be smaller. A neurosurgical skull grinding water-catching grinding tool is based on the above analysis. The grinding tool is made of 420b or 630 stainless steel, which is the most widely used material in present clinical skull surgery, and the Young's contact angle between the material and water-based liquid is 85°, that is, the material itself has weak hydrophilicity, and is more favorable for preparing a super-hydrophilic surface. FIG. 16 shows a grinding head base of the water-catching grinding tool and a cross-sectional view. As shown in FIG. 16, the grinding head base 202 is composed of eleven octagonal cylinders 202-2 and a partial sphere 202-1, the octagonal cylinders 202-2 are spliced vertically in sequence, the partial sphere 202-1 is arranged at the top of the octagonal cylinders and connected with the grinding tool handle 201, and the edges of the octagonal cylinders and the partial sphere are distributed on a circle having a radius $R_1$.

Figure 17:
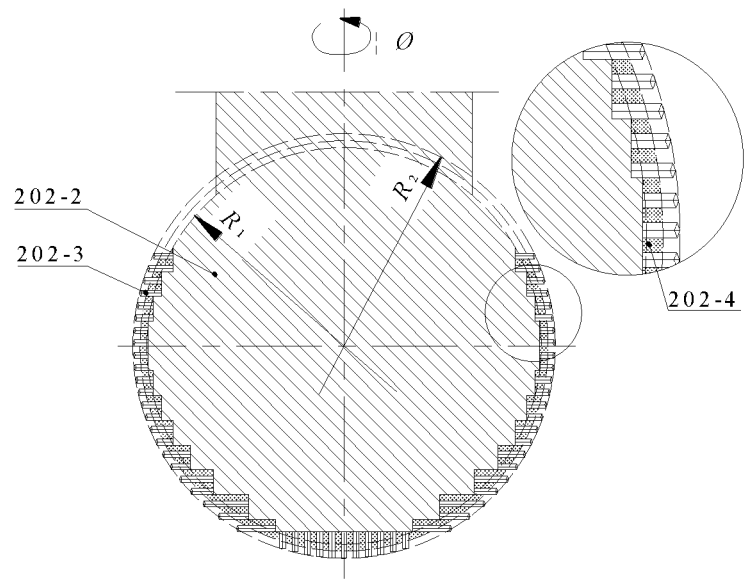

It can be known from equation (20) that when the side length and spacing of the micro-bulges are constant, the nanofluid droplets can be more hydrophilic by improving the height of the micro-bulges. The microstructure of the grinding head base is designed as shown in FIG. 17, the rotation speed of the grinding tool is ω, square columnar micro-bulges 202-3 are uniformly distributed on each octagonal cylinder, and the edges of the bulges 202-3 are distributed on a circle having a radius $R_2$. The micro-bulges 202-3 having a feature size of micron-scale also serve as abrasive grains to cut the bone material while adhering nanofluid droplets, and the edges of the square columns are cutting edges. The micro-bulges are arranged on the surface of the base by soldering.

An aqueous dispersion of a water-soluble polymer and a water-insoluble polymer is applied to the 420b (or 630) stainless steel surface by drop casting and dried. During the drying process, the water-soluble polymer and the water-insoluble polymer undergo phase separation to form a nano separator on the 420b stainless steel and form a non-nano separator film on the nano separator. The non-nano separator film is washed away with deionized water to obtain a nano separator film 202-4. Due to the intermolecular rearrangement, the nano separator film 202-4 is tightly adhered between the micro-bulges 202-3 on the surface of the grinding head base 202. The nano separator film 202-4 has super-hydrophilic property and strong water catching ability. Therefore, the nano-thickness nano separator film 202-4 can convert the 420b stainless steel surface into a super-hydrophilic surface while having a property of capturing a medical nanofluid coolant water film.

Figure 18:
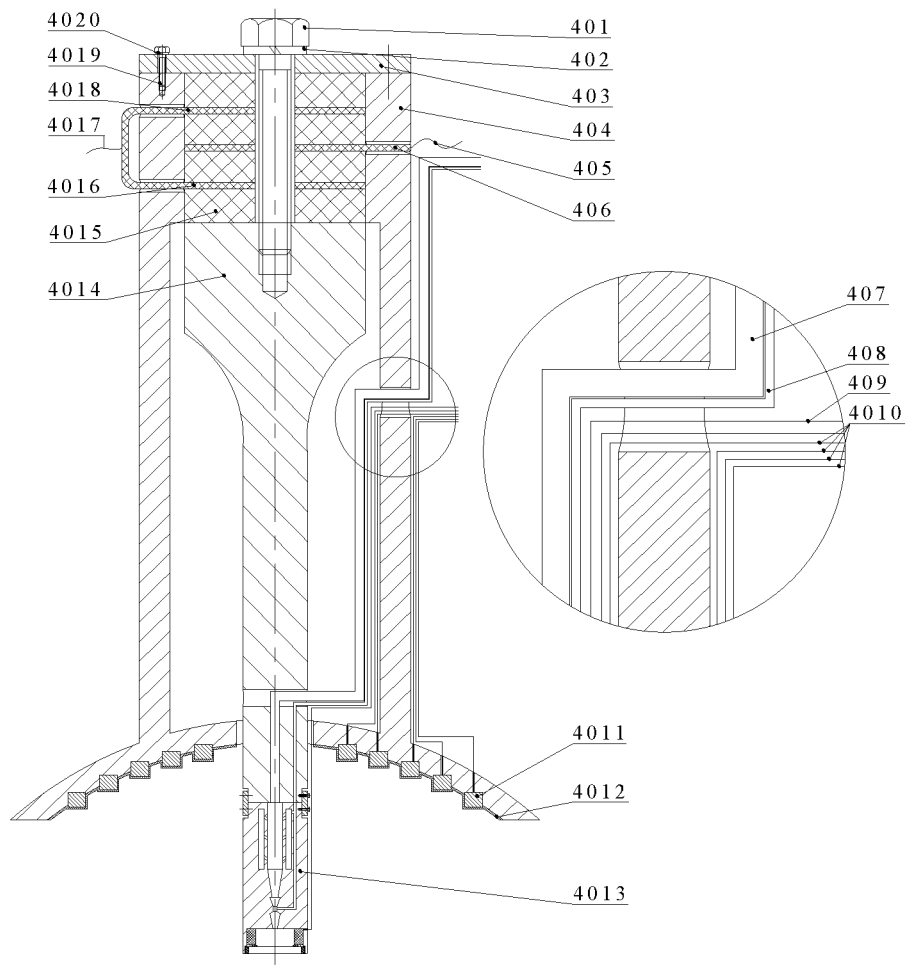

As shown in FIG. 18, a top cover I 403, piezoelectric ceramic plates II 4015, an electrode plate IV 406, an electrode plate V 4016 and an electrode plate VI 4018 are closely connected with a horn II 4014 through a center screw II 401 and a spring washer VI 402. A spherical crown transducer housing 404, the electrode plate V 4016, the piezoelectric ceramic plates II 4015, the electrode plate VI 4018 and the electrode plate IV 406 constitute a transducer. During operation, the ultrasonic generator 5 converts alternating current into high-frequency electric oscillation signals, which are respectively transmitted to the electrode plate IV 406, the electrode plate V 4016 and the electrode plate VI 4018 through an electric excitation signal line I 405 and an electric excitation signal line III 4017, the high-frequency electric oscillation signals are converted into an axial high-frequency vibration, and the horn II 4014 is closely connected with the piezoelectric ceramic plates II 4015 to amplify the amplitude so as to implement ultrasonic cavitation on the nanofluid. The spherical crown transducer housing 404 is tightly connected with the top cover I 403 by screws V 4019 and spring washers VII 4020.

Figure 21:
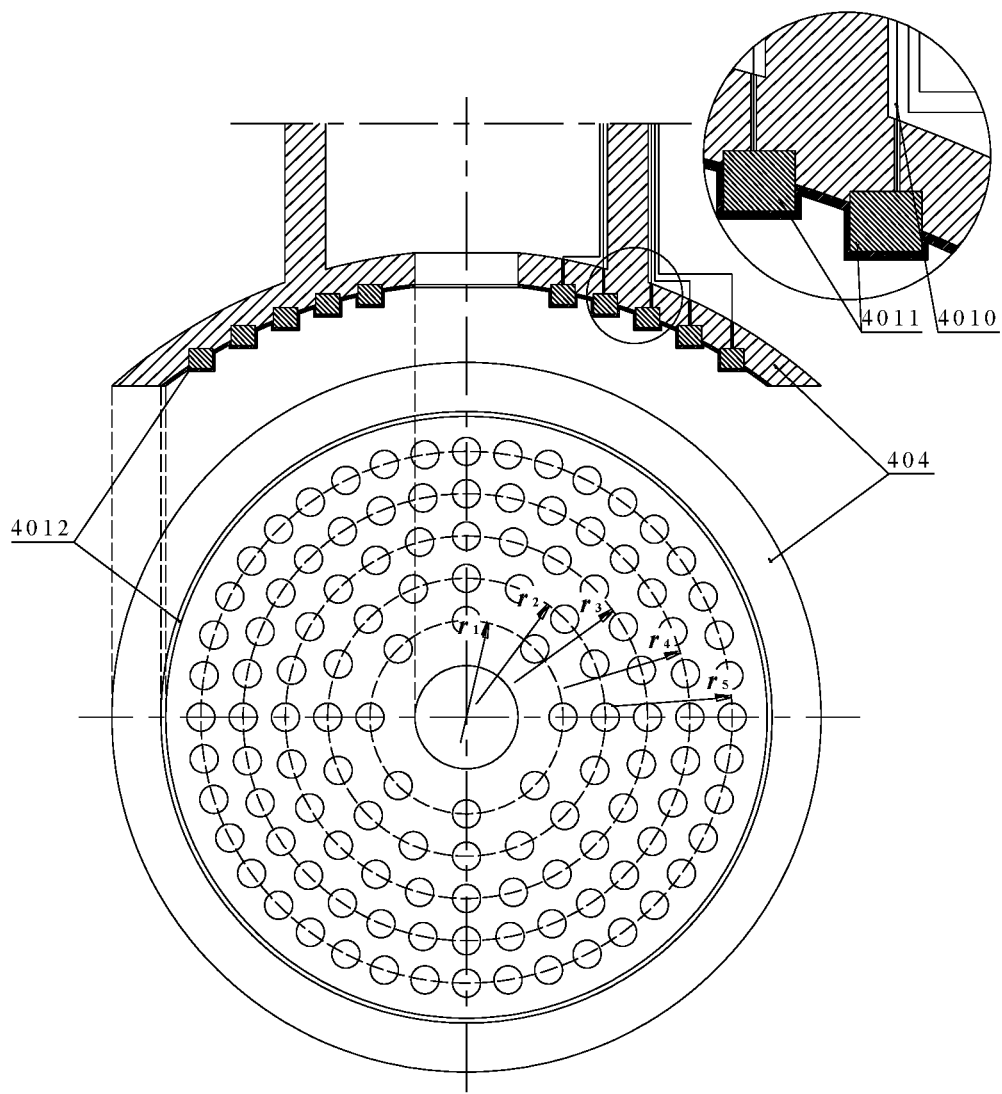

As shown in FIGS. 19 and 20, a threaded hole VI 4013-1 and a threaded hole VII 4013-12 are machined at the upper end of the electrostatic atomizing nozzle 4013, and the electrostatic atomizing nozzle 4013 is fixed at the lower end of the horn II 4014 by a connecting plate I 4021 and a connecting plate II 4026 through a screw VI 4022, a screw VII 4024, a spring washer VIII 4023 and a spring washer IX 4025. FIG. 21 shows a cross-sectional view of the electrostatic atomizing nozzle. The nozzle body is complicated in structure and difficult to manufacture and is required to have certain insulating property, so the nozzle body is manufactured using a ceramic material through a rapid molding process. Compressed gas entering from a compressed gas inlet 4013-14 passes through an internal compressed gas passage 4013-3 and a swirling compressed gas passage 4013-11 to enter a mixing chamber at a set tangential velocity, and is mixed with a nanofluid entering from a nanofluid inlet 4013-13 to form a three-phase flow of high pressure gas, normal saline and solid nanoparticles. The three-phase flow is accelerated by an acceleration chamber 4013-5, then enters a vortex chamber 4013-6 and forms vortex therein together with compressed air entering through a vortex chamber compressed gas passage 4013-4, and the three-phase flow is further mixed and then ejected through an outlet of a nozzle body 4013-2 to form droplets. The ejected droplets pass through a drift region of corona discharge of needle electrodes 4013-9, collide with drifting electrons and are charged, and the charged droplets are controllably sprayed to the surface of a workpiece under the action of electric field force, pneumatic pressure and gravity.

The electrode tray 4013-8 is made of an insulating material, and a high voltage inlet hole 4013-7 is arranged in the electrode tray 4013-8. As shown in FIG. 20, eight electrode slots are circumferentially arrayed in the electrode tray 4013-8, the needle electrodes 4013-9 (in interference fit with the electrode slots, clamped by the elastic deformation force of the insulating material) are mounted in the electrode slots, and the respective needle electrodes 4013-9 are connected in series by a high voltage wire 409 and led out via a leading-out through hole of the high voltage wire tray. A positioning threaded ring 4013-10 mainly plays a role in positioning the electrode tray 4013-8.

Electrostatic Atomization Mechanism:

When there is a high relative velocity between the droplets and the surrounding gas, the splitting of the droplets is controlled by pneumatic pressure, surface tension and viscous force. For liquid having low viscosity, the breakage of the droplets is mainly determined by the pneumatic pressure and the surface tension. The pneumatic pressure borne by large droplets is $0.5\rho_g \Delta V^2$, wherein $\rho_g$ is the density of gas and $\Delta V$ is the gas-liquid relative velocity. However, the cohesive force generated by the surface tension will hinder the deformation and breakage of the droplets, and the cohesive force can be expressed as $4\sigma/D$, wherein $\sigma$ is the inherent surface tension of liquid, and D is the initial diameter of droplets. When the diameter of the droplets is reduced, the cohesive force is increased. When the cohesive force and the tensile stress caused by the pneumatic pressure are balanced, the droplets remain stable, and if they cannot cancel each other, the droplets will be deformed or even broken. According to the principle that the tensile stress generated by the pneumatic pressure acting on the droplets and the cohesive force generated by the surface tension are balanced, a dimensionless number can be obtained:

$$We = \frac{\rho_g \Delta V^2 D}{\sigma} = 8 \tag{22}$$

It can be seen that when We is more than 8, the droplets are unbalanced in stress and deformed. In addition, a maximum steady-state droplet diameter corresponding to $\Delta V$ can be solved according to (22):

$$D_{max} = \frac{8\sigma}{\Delta V^2 \rho_g} \tag{23}$$

Under the action of Coulomb repulsion, the surface tension of the charged droplets becomes weak, and the weakened surface tension value is:

$$\sigma' = \sigma - \frac{q^2}{64\pi^2 \varepsilon r^3} \tag{24}$$

in which: r is the radius of a droplet; q is the charged quantity of the droplet; and $\varepsilon$ is a dielectric constant of the surrounding air. It can be seen from equation (24) that when the charge quantity q is increased, the surface tension is lowered, so the charged surfaces of the droplets contribute to atomization. At this moment, We of the charged droplets can be expressed as:

$$We = \frac{\rho_g \Delta V^2 D}{\sigma - \frac{q^2}{64\pi^2 \varepsilon r^3}} = \frac{128\pi^2 \varepsilon R^4 \rho_g \Delta V}{64\pi^2 \varepsilon R^3 \sigma - q^2} \tag{25}$$

It can be seen from equation (25) that the breakage of the charged droplets in the high-speed gas flow is closely related to a gas-liquid relative velocity, gas-liquid physical parameters and a charging field. In addition, if the droplets reach a steady state in the gas flow, after the droplets are charged with static electricity, the number We increases, the surface tension of the liquid decreases and is insufficient to resist the pneumatic pressure, and the droplets will be further deformed and broken, so the diameters of the droplets charged with static electricity are smaller under the same gas-liquid parameters, and the purpose of thinning the droplets is achieved; at the same time, the same charge on the surfaces of the droplets can ensure more uniform distribution of the droplets. Therefore, the device can realize pneumatic and ultrasonic atomization and then electrostatic atomization, totally three levels of atomization, finally obtaining superfine droplets distributed uniformly.

As shown in FIGS. 21, 8, 16, 24, 32 and 40 circular holes are respectively distributed on concentric circles $r_1$, $r_2$, $r_3$, $r_4$ and $r_5$ around the center, plane wafer piezoelectric elements 4011 are nested and adhered in the circular holes, and all the plane wafer piezoelectric elements 4011 have the same diameter and thickness. A copper mesh common electrode 4012 covers the lower ends of the plane wafer piezoelectric elements 4011 and is adhered to all the plane wafer piezoelectric elements 4011 with an adhesive, and the bottom surface of the spherical crown portion is pressed by a pressure table, so that the adhered ends of the copper mesh common electrode 4012 and the plane wafer piezoelectric elements 4011 are flattened. The upper surfaces of all the plane wafer piezoelectric elements 4011 on the circles having the radii of $r_1$, $r_2$, $r_3$, $r_4$ and $r_5$ are connected into a line by electric excitation signal lines II 4010, and they are excited by a power supply independently to form a branch.

The Westervelt sound wave propagation equation is:

$$\nabla^2 p - \frac{1}{c_0^2}\frac{\partial^2 p}{\partial t^2} + \frac{\delta}{c_0^4}\frac{\partial^3 p}{\partial t^3} + \frac{\beta}{\rho_0 c_0^4}\frac{\partial^2 p^2}{\partial t^2} = 0 \tag{26}$$

in which: $\nabla$ is a Laplacian operator; p is sound pressure; $c_0$ and $\rho_0$ are respectively sound velocity and density of a medium; $\beta=1+B/(2A)$ is a nonlinear coefficient of sound waves, and B/A is a nonlinear coefficient of a fluid medium; $\delta=2c_0^3 \alpha/\omega^2$ is a sound wave diffusion coefficient; $\alpha$ is an absorption coefficient; $\omega=2\pi f$ is an angular frequency; and f is a frequency.

The central difference is performed on equation (26) by adopting a time domain finite difference method. The difference equation is:

$$p^{n+1}(i, j, k) = \frac{1}{H}\left[c_0^2(dt)^2 \nabla^2 p + H_1 p^n(i, j, k) - H_2 p^{n-1}(i, j, k)\right] + \tag{27}$$

$$\frac{H_3}{H}[34 p^{n-2}(i, j, k) - 24 p^{n-3}(i, j, k) +$$

$$8 p^{n-4}(i, j, k) - p^{n-5}(i, j, k)]$$

in which, $$H = 1 - \frac{4\beta}{\rho c_0^2} p^n(i, j, k) + \frac{2\beta}{\rho c_0^2} p^{n-1}(i, j, k)$$

-continued $$H_1 = 2 + \frac{3\delta}{c_0^2 dt} - \frac{6\beta}{\rho c_0^2} p^n(i,j,k) + \frac{4\beta}{\rho c_0^2} p^{n-1}(i,j,k),$$

$$H_2 = 1 + \frac{23\delta}{2c_0^2 dt},$$

$$H_3 = \frac{\delta}{2c_0^2 dt};$$

i, j and k are coordinates in three coordinate axes x, y and z under a rectangular coordinate system; dx, dy and dz respectively represent spatial step sizes in the three coordinate axes x, y and z; dt is a time step; n is a calculation time.

Figure 22:
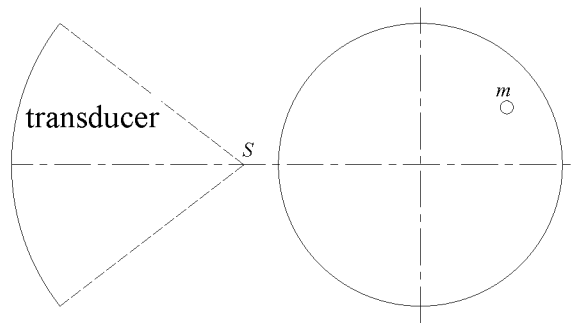

As shown in FIG. 22, a sinusoidal point source $S_0(t)$ is set at a target focus S, a sound pressure signal $S_{0m}(t)$ transmitted to the center point of an array element m of a phased array is obtained by numerical simulation, and the signal is reversed in a time series to obtain a signal $S_{0m}(T-t)$ corresponding to the array element m. A relative initial phase delay $\Delta t_m$ of $S_{0m}(T-t)$ within a period of time is calculated using least squares function fitting, and then the amplitude of the sinusoidal signal is modulated using the same input sound intensity. The excitation signal of the array element m is:

$$S_{0m}(t) = P_0 \sin(\omega(t+\Delta t_m)) \tag{28}$$

The phase of each array element is controlled by controlling the array element excitation signal, so that the sound beam of each array element reaching a certain point (set focus) of the space has the same phase. Continuous and dynamic adjustment on the size and position of the focus is finally realized by controlling the shape of sound beams, the distribution of sound pressure and the angles of the sound beams.

Figure 23:
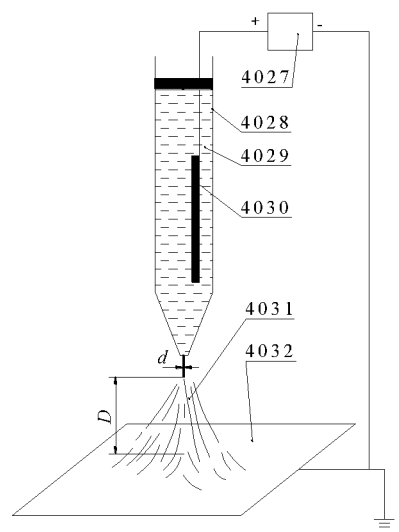

FIG. 18 shows a cross-sectional view of a three-level atomization focus adjustable ultrasonic focusing nozzle, and FIG. 23 is a principle diagram of spinning. As shown, the spinning medium 4029 is a polymer solution or melt and is filled in an injection pump 4028, and a metal electrode 4030 is inserted therein. The electrode is connected with a high-voltage electrostatic generator 4027 to charge the liquid. A grounded receiving plate 4032 serves as a cathode. When the electric field is not activated, a continuous and constant thrust is applied to a piston by the injection pump 4028, and the spinning medium 4029 in the injection pump 4028 is extruded onto the needle at a fixed rate. When the high-voltage electric field is not activated, the spinning solution forms droplets suspended on the nozzle under the synergistic action of self-gravity, self-viscosity and surface tension. When the electric field is activated, charges are generated on the surface of the polymer solution, and mutual repulsion of the charges and compression of opposite charged electrodes on surface charges both generate a force opposite to the surface tension. When the voltage is not high enough, the surface tension on the surface of the droplets will prevent the droplets from being ejected but holds them at the nozzle. When the applied voltage increases, the hemispherical surface of the droplet to be dropped will be twisted into a cone. When the applied voltage continues to increase and exceeds a critical value, the charged portion in the solution overcomes the surface tension of the solution to form a charged jet and the charged jet is ejected from the nozzle. Under the action of the electric field, when the fiber jet 4031 is stretched to a certain extent, bending and further split stretching phenomena occur, at this time, the solvent is rapidly volatilized due to the rapid increase of the specific surface area of the jet 4031, and finally, the jet is collected on a collection net and cured into a nonwoven fabric fiber mat. The high-voltage electrostatic generator 4027 is usually supplied with a high voltage of 5 to 20 kV. In addition, the positive voltage field is beneficial to the release of charges on the surface of the fiber, while the negative voltage field provides a relatively stable electric field force, and the two have difference influence on electrostatic atomized film formation of different polymers.

The basic theory of electrospinning:

After the charged droplets are introduced into the electric field, the charges accumulate on the surface of the droplets, thereby generating a charge repulsion (represented as electrostatic pressure $P_E = \sigma^2/2\varepsilon_0$ on the surface of the charged droplets, related to the density $\sigma$ of charges on the surface of the droplets and a dielectric constant $\varepsilon_0$ in vacuum) that drives the droplets to split outward. The charge repulsion and the surface tension (represented as $PC = 2\gamma/R$ related to liquid surface tension $\gamma$ at the tail end of the nozzle and the radius R of the droplets) which tends to shrink the droplets on the surface of the droplets form an unsteady balance that can be expressed as:

$$\Delta P = 2\gamma/R - e^2/(32\varepsilon_0 \Pi^2 R^4) \tag{29}$$

in which, e is the total charges carried by the droplets; and R is the radius of the droplets. It can be seen, as the radius of the droplets decreases (the charge density increases), the pressure generated by the static electricity increases. When the tension generated on the surface of the droplets is equal to the electrostatic repulsion, the charged droplets in the electric field are balanced. It is assumed that the diameter of the charged droplets is D, which is converted into the charge density on the surface of the droplets, the following equation can be obtained:

$$e/M = \sqrt{[(288\varepsilon_0 \gamma)/(\rho^2 D^3)]} \tag{30}$$

in which, M is the mass of a droplet.

When the charge repulsion exceeds this limit, the droplet at the end of the nozzle splits into a plurality of small droplets, forming an electrostatic atomization phenomenon. This limit of droplet stabilization is called "Rayleigh stability limit". If the liquid jet is cylindrical, the condition of "Rayleigh stability limit" can be expressed by the following equation:

$$\Delta P = \gamma/R - \tau^2/(\varepsilon 8_0 \pi^2 R^4) \tag{31}$$

in which, $\tau$ indicates charges carried by a liquid jet length unit and is converted into the charge density of the jet surface:

$$e/M = V[(64\varepsilon_0 \gamma)/(\rho^2 D^3)] \tag{32}$$

It can be seen from the above equation that when the condition of "Rayleigh stability limit" is satisfied, less charges are needed to form a cylindrical jet on the surface of a Taylor cone with respect to electrostatic atomization, which has a special example: electrospinning.

The formula for calculating the critical voltage of the jet from the top of the Taylor cone is:

$$V^2c = (4 H^2/L^2) \cdot [ln(L2R/) - 1.5] \cdot (0.117 \Pi \gamma R_0) \tag{33}$$

in which: H is the distance between two electrodes; L is the distance that the nozzle extends out of a polar plate; R is the radius of a suspended droplet; R0 is the radius of the nozzle.

The forces borne by the surface of the suspended droplet mainly include electric field force, viscous stress, hydrostatic pressure difference, and pressure difference caused by the surface tension. When the tangential electric field force on the surface of the suspended droplets is greater than the tangential viscous stress, a single jet or multiple jets are formed; otherwise, droplets are formed.

Figure 24:
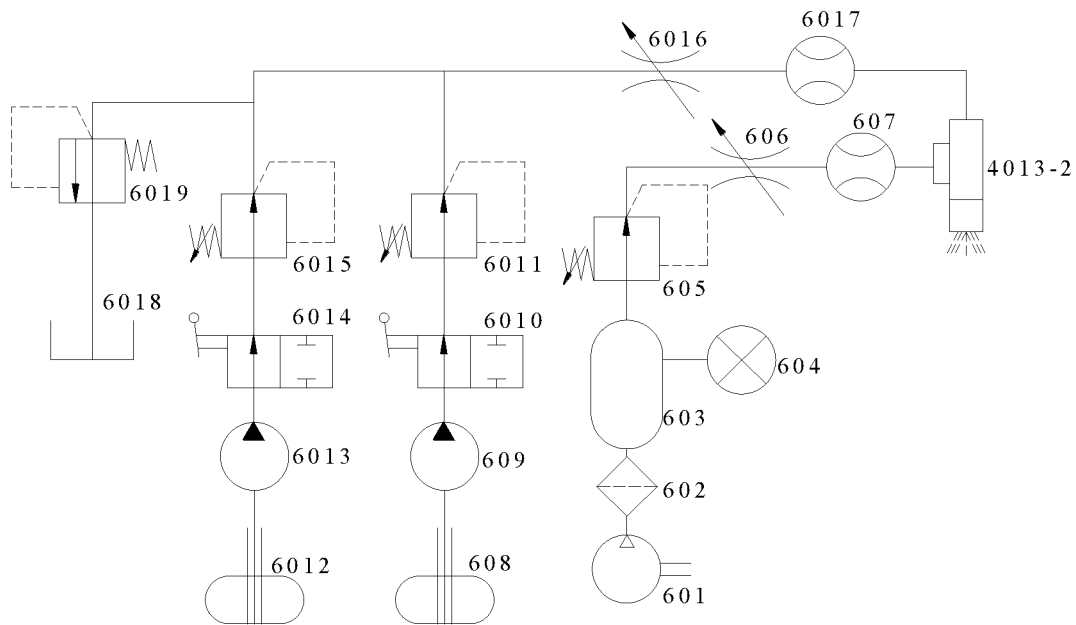

As shown in FIG. 19, when a medical nanofluid is stored in the liquid storage cup 6, the nanofluid can be pneumatically and ultrasonically atomized and then electro-statically atomized to obtain superfine droplets distributed uniformly for effectively cooling and lubricating the grinding zone. When an electrospinning system applied to wound dressing is stored in the liquid storage cup 6, superfine fibers can be obtained in the same way to coat a postoperative wound. FIG. 24 shows a liquid path and gas path system of the device. The liquid path (nanofluid) of the cooling and film forming mechanism is composed of a liquid storage cup I 608, a hydraulic pump I 609, a pressure regulating valve II 6011, a throttle valve II 6016 and a turbine flow meter II 6017 connected in sequence; the liquid path (spinning medium) of the film forming device is composed of a liquid storage cup II 6012, a hydraulic pump II 6013, a pressure regulating valve III 6015, a throttle valve II 6016 and a turbine flow meter II 6017 connected in sequence; and the gas path is composed of an air compressor 601, a filter 602, a gas tank 603, a pressure regulating valve I 605, a throttle valve I 606 and a turbine flow meter I 607 connected in sequence. During operation, the hydraulic pump is started, and the fluid stored in the liquid storage tank enters a nanofluid inlet 4013-13 of the nozzle body 4013-2 via the fluid pressure regulating valve, the fluid throttle valve and the turbine flow meter. The overflow valve 6019 functions as a safety valve. When the pressure in the liquid path exceeds a set pressure, the overflow valve 6019 is opened to allow the coolant to flow back to a recovery tank 6018 via the overflow valve 6019. The nanofluid (or spinning medium) flows out of the turbine flow meter II 6017 and then enters the liquid inlet pipe 407 (FIG. 18), enters the internal nanofluid inlet 4013-13 (FIG. 20) of the nozzle body via the internal liquid inlet passage II 4014 (FIG. 19) of the horn II 4014, and is ejected from the nozzle body 4013-2 after three-level atomization.

When the hydraulic pump is started, the air compressor 601 is started, high pressure gas enters the compressed gas inlet 4013-14 of the nozzle body 4013-2 via the filter 602, the gas tank 603, the gas pressure regulating valve I 605, the gas throttle valve I 606 and the gas turbine flow meter I 607, and a pressure gauge 604 monitors the pressure value in the gas path. The compressed gas flows out of the turbine flow meter I 607 and then enters the air inlet pipe 408 (FIG. 18), enters the internal compressed gas inlet 4013-14 (FIG. 20) of the nozzle body via the internal air inlet passage 4014-2 (FIG. 19) of the horn II 4014, and is mixed with the nanofluid, and the mixture is ejected from the nozzle body 4013-2.

During the operation, the reversing valve II 6014 is at a normal position, the liquid path of the liquid storage cup II 6012 is not opened; the reversing valve I 6010 is at a working position, and the liquid path of the liquid storage cup I 608 works normally; after the operation is finished, the reversing valve I 6010 is closed, the reversing valve II 6014 is opened, and the liquid path of the liquid storage cup II 6012 works. The pressure and flow rate of the nanofluid (or spinning medium) and the high pressure gas can achieve an optimal micro-lubrication effect as needed by adjusting the pressure regulating valves, the throttle valves and the flow meters in the gas path and the liquid path.

Figure 25:
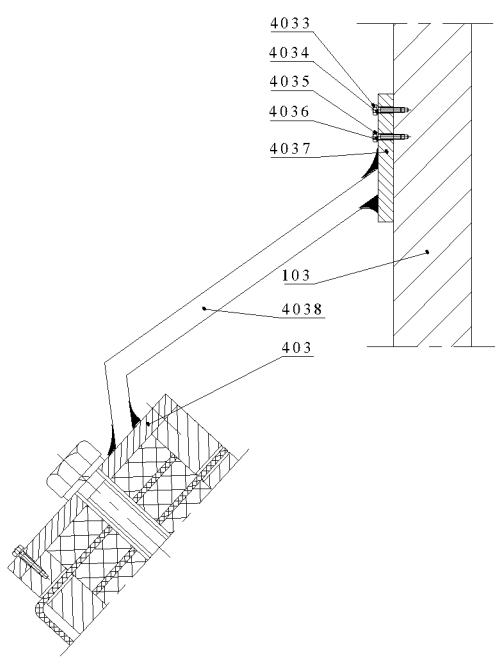

As shown in FIG. 25, one end of a connecting rod 4038 is welded on the top cover I 403, and the other end is welded on the connecting plate III 4037. The electric spindle housing 103 is machined with a threaded hole IV 1026 and a threaded hole V 1027. The cooling and film forming mechanism is fixed on the electric spindle housing 103 by a screw VIII 4033, a spring washer X 4034, a screw IX 4035, a spring washer XI 4036, a connecting plate III 4037 and a connecting rod 4038.

Figure 26:
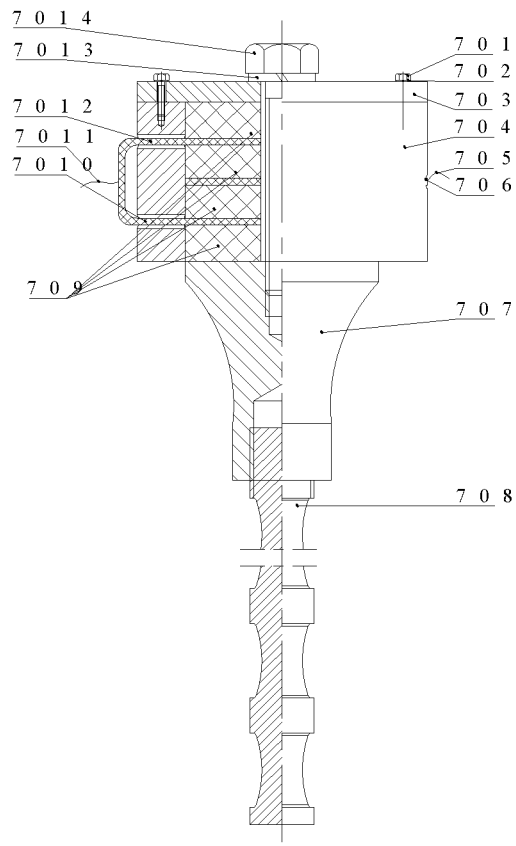

FIG. 26 is a half cross-sectional view of the ultrasonic vibration bar. A center screw III 7014 and a spring washer XIII 7013 fasten a top cover II 703, piezoelectric ceramic plates III 709, an electrode plate VII 706, an electrode plate VIII 7010 and an electrode plate IX 7012, and a transducer housing 704 is fixed on the top cover II 703 via screws X 701 and spring washers XII 702. During operation, the ultrasonic generator 5 converts alternating current into high-frequency electric oscillation signals and transmits them to the electrode plate VII 706, the electrode plate VIII 7010 and the electrode plate IX 7012 through an electric excitation signal line IV 705 and an electric excitation signal line V 7011 respectively, the high-frequency electric oscillation signals are converted into an axial high-frequency vibration, and the amplitude is amplified by a horn III 707. The horn III 707 is fastened with a vibration bar 708 by threads, and transfers the amplified vibration to the vibration bar 708 to ultrasonically oscillate the medical nanofluid (or medical spinning medium) in the liquid storage cup 6.

The ultrasonic vibration bar 7 performs ultrasonic oscillation on the spinning system in the liquid storage cup 6, thereby effectively reducing the viscosity of the electrospinning solution and melt, expanding the electrospinning concentration range of the device, but also effectively reducing the diameters of fibers, reducing the structural defects of the fibers, and improving the mechanical properties of the spinning fibers. As shown in FIG. 21, ultrasonic waves of certain power are applied during fiber formation, so that the fibers can be stretched under the action of jet flow to achieve the purpose of further thinning, at the same time, the ultrasonic effect can improve the fluidity of the polymer solution, improve the spinnability and accelerate the process of solidification of the fibers.

The longitudinal torsional resonant rotary ultrasonic electric spindle 1 realizes longitudinal-torsional and rotary motions of horns, and the water-catching grinding tool 2 installed can remove pathological bone tissues safely and efficiently with the aid of the endoscope 3; the cooling and film forming mechanism 4 performs pneumatic-ultrasonic-electrostatic three-level atomization on the nanofluid, and the nanofluid is finally flushed to the grinding zone in the form of droplets under the action of ultrasonic focusing for effective cooling and lubrication; and at the same time, the nanofluid coats the postoperative wound to prevent wound infection.

Figure 27:
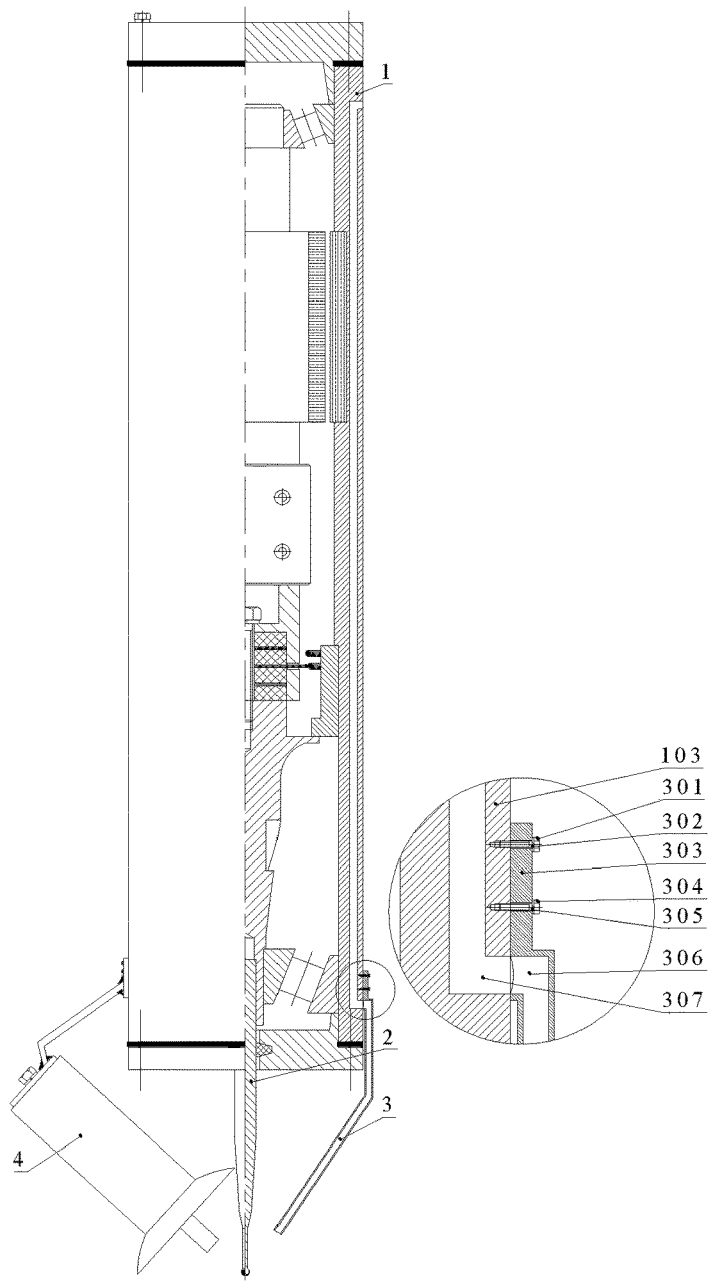
Figure 28:
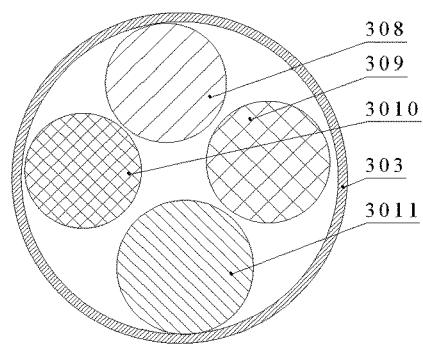

FIG. 27 shows an installation diagram of the endoscope in the electric spindle housing. The electric spindle housing 103 is machined with a threaded hole II 1019 and a threaded hole III 1020. The endoscope body 303 is fixed on the electric spindle housing 103 by a screw III 301, a spring washer IV 302, a screw IV 304 and a spring washer V 305. A fiber channel II 307 is arranged inside the electric spindle housing 103, and a fiber channel I 306 is arranged inside the endoscope body 303. FIG. 28 shows a cross-sectional view of the interior of the endoscope body. A cold light illumination source transmission fiber 308, an endoscope fiber 309, a fluorescence excitation light transmission fiber 3010 and an image transmission fiber 3011 are arranged independently with each other in the endoscope. The fluorescence excitation light can excite tumor tissues to emit fluorescence of a corresponding wavelength, the fluorescence emitted light passes through the endoscope fiber 309 and the image transmission fiber 3011, and the fluorescence emitted light can be seen through an eyepiece, so that tumor tissues are accurately identified. The image transmission fiber 3011 is connected to a monitor, thereby facilitating excision of identifiable tissues with surgical instruments under the illumination of the fiber to achieve the purpose of therapy. Since the endoscope 3 is closely connected with the longitudinal torsional resonant rotary ultrasonic electric spindle 1, a surgeon can conveniently and flexibly realize the operation of any pose in real time with the aid of the endoscope 3, and realize flexible removal of skull base tumors.

The specific working process of this solution is as follows:

According to an electrostatic atomization ultrasonic aided low-damage and controllable biologic bone grinding device, the longitudinal torsional resonant rotary ultrasonic electric spindle 1 can realize longitudinal-torsional and rotary motions of the grinding tool, which is beneficial to timely discharge of bone debris and achieves high grinding efficiency; the grinding tool is a water-catching grinding tool 2, square columnar micro-bulges are regularly arranged on the grinding head, and the surface of the grinding head base is treated to obtain a nano separator film with strong water-catching ability and super hydrophilicity, thereby enhancing the convective heat exchange in the grinding zone; the cooling and film forming mechanism 4 performs pneumatic-ultrasonic-electrostatic three-level atomization on the medical nanofluid coolant to obtain superfine droplets, and the nanofluid droplets are injected into the grinding tool/bone wedge-shaped constraint space by ultrasonic focusing to effectively cool and lubricate the grinding zone; and after the operation, the spinning system applied to wound dressing is sprayed onto the postoperative wound surface in the form of spinning fibers after three-level atomization to achieve atomized film forming protection on the ground wound surface. The device can be used for implementing removal of skull base tumors under the endoscope, intraoperative cooling and postoperative wound film formation, and is high in integration, high in grinding removal efficiency and low in grinding temperature, that is, low-damage and controllable grinding of a biologic bone can be realized using one device.

When the device is used, the conical roller bearing II 1034 is positioned by the end cover I 101 and the shoulder of the spindle 104, and the conical roller bearing II 1034 is installed at one end of the spindle 104 by the positioning device. The electrode plates and the piezoelectric ceramic plates are installed in the connecting cylinder 1011 by the center screw I 1033 and the spring washer II 1032, and the connecting cylinder 1011 is connected with the spindle 104 through the coupling 109 and the threaded hole I 1010. The end covers play a role in axial positioning of bearings, dust proofing and sealing. The end cover I 101 is installed at the top of the electric spindle housing 103 through the spring washers III 1036 and the screws II 1035, the spindle 104 and the connecting cylinder 1011 assembled are installed within the electric spindle housing 103 according to the positions, and the sleeve 1016 is installed within the electric spindle housing 103 according to the position. The conical roller bearing I 1018 is positioned by the shoulder of the horn I 1017 and the end cover II 1022, the conical roller bearing I 1018 is installed at one end of the horn I 1017 according to the position, and the prepared water-catching grinding tool 2 is installed at the end of the horn I 1017 by threaded connection. The horn I 1017 is connected with the end of the center screw I 1033 in the electric spindle housing 103 through the threaded hole in the top of the horn I 1017. After being coated with lubricating grease, the end cover II 1022 is installed at the end of the electric spindle housing 103 by the screws I 1025 and the spring washers I 1024. The threaded hole at the upper end of the horn I 1017 is fastened with the center screw I 1033, the threaded hole at the lower end is fastened with the grinding tool handle 201, and the thread directions of the two threaded connections are opposite to the direction of rotation, thereby ensuring the connection tightness.

8, 16, 24, 32 and 40 uniform circular holes are respectively machined on concentric circles $r_1$, $r_2$, $r_3$, $r_4$ and $r_5$ around the center of the spherical crown transducer housing, plane wafer piezoelectric elements 4011 are nested and adhered in the circular holes, and all the plane wafer piezoelectric elements 4011 have the same diameter and thickness. The copper mesh common electrode 4012 is adhered to the lower ends of all the plane wafer piezoelectric elements 4011 with an adhesive, and the bottom surface of the spherical crown portion is pressed by a pressure table, so that the adhered ends of the copper mesh common electrode 4012 and the plane wafer piezoelectric elements 4011 are flattened. The electrostatic atomizing nozzle 4013 is installed at the end of the horn II 4014 by a screw VI 4022, a spring washer VIII 4023, a screw VII 4024, a spring washer IX 4025 and a connecting plate I 4021. The spherical crown transducer housing 404, the electrode plate V 4016, the piezoelectric ceramic plates II 4015, the electrode plate VI 4018 and the electrode plate IV 406 constitute a transducer. The top cover I 403, the electrode plates and the piezoelectric ceramic plates are sequentially stacked, then installed on the transducer together with the horn II 4014 through the center screw II 401 and the spring washer VI 402, and fastened by the spring washers VII 4020 and the screws V 4019. The electric excitation signal lines II 4010, the liquid inlet pipe 407, the air inlet pipe 408 and the high voltage wire 409 are respectively connected to the corresponding positions, and finally, the assembled cooling and film forming mechanism is welded to the electric spindle housing 103 by the connecting rod 4038.

Before an operation, the power interface I 105, the power interface II 1013 and the ultrasonic generator 5 are simultaneously started. When the water-catching grinding tool 2 achieves stable rotation and longitudinal torsional vibration, the reversing valve I 6010 is opened, the cooling and film forming mechanism works, the medical nanofluid is ejected from the nozzle body 4013-2 in the form of droplet jet and enters the grinding zone for efficient cooling and lubrication, the endoscope system 3 is opened, and the surgery begins with the aid of the endoscope. After the grinding is completed, the reversing valve I 6010 is closed, the reversing valve II 6014 is opened, the film forming device works, and the postoperative wound is coated with spinning fibers. After the operation, all power is turned off, the water-catching grinding tool 2 is detached, and the device is disinfected and kept in a safe place.

Described above are merely preferred embodiments of the present application, and the present application is not limited thereto. Various modifications and variations may be made to the present application for those skilled in the art. Any modification, equivalent substitution, improvement or the like made within the spirit and principle of the present application shall fall into the protection scope of the present application.

The invention claimed is:

1. An electrostatic atomization ultrasonic aided low-damage and controllable biologic bone grinding device, comprising:
a spindle, arranged rotatably;
a water-catching grinding tool for grinding a biologic bone, the spindle being connected with the water-catching grinding tool through an ultrasonic vibration mechanism, and the water-catching grinding tool achieving longitudinal and rotary motions under a drive of the spindle and the ultrasonic vibration mechanism;
a cooling and film forming mechanism, arranged on a first side of the water-catching grinding tool and connected with an ultrasonic generator in the ultrasonic vibration mechanism, a nozzle connected with a medical nanofluid storage cup being arranged at a bottom of the cooling and film forming mechanism, compressed gas capable of being introduced into the nozzle to perform pneumatic-ultrasonic atomization on a medical nanofluid, and then the nanofluid being flushed into a grinding zone in a form of droplets for effective cooling and lubrication; and
an endoscope, arranged on a second side, opposite to the first side, of the water-catching grinding tool.

2. The electrostatic atomization ultrasonic aided low-damage and controllable biologic bone grinding device according to claim 1, wherein the cooling and film forming mechanism comprises a transducer housing, in which a horn is arranged, four piezoelectric ceramic plates are arranged at the a top of the horn, and an electrode plate connected with an ultrasonic generator is arranged between two adjacent piezoelectric ceramic plates.

3. The electrostatic atomization ultrasonic aided low-damage and controllable biologic bone grinding device according to claim 2, wherein a liquid inlet passage and an air inlet passage are arranged in the horn, the liquid inlet passage communicates with a nanofluid inlet of the nozzle, and the air inlet passage communicates with a compressed gas inlet of the nozzle;
or a nanofluid passage and a compressed gas passage are arranged in the nozzle, an internal compressed gas passage communicating with the nanofluid passage is also arranged in the nozzle, an acceleration chamber is arranged at a bottom of the nanofluid passage, and the compressed gas passage communicates with the acceleration chamber;
or the acceleration chamber comprises a first reducing section and a second reducing section communicating with each other, wherein the first reducing section and the second reducing section are both in a shape of a reverse circular truncated cone, the second reducing section is connected with a third section through a cylinder section, and the third section is a vortex chamber.

4. The electrostatic atomization ultrasonic aided low-damage and controllable biologic bone grinding device according to claim 2, wherein a bottom of the transducer housing is of a hemispherical structure, a plurality of wafer piezoelectric elements connected with the ultrasonic generator are arranged inside the hemispherical structure, and a copper mesh common electrode is arranged on a surface of the wafer piezoelectric elements;
or the wafer piezoelectric elements are arranged, in the form of a plurality of concentric circles, on circumferences of the plurality of concentric circles.

5. The electrostatic atomization ultrasonic aided low-damage and controllable biologic bone grinding device according to claim 1, wherein an electrode supported by an electrode tray is arranged inside the nozzle, and the electrode is connected with a high-voltage electrostatic generator to charge medical nanofluid droplets at the nozzle so as to further refine the nanofluid.

6. The electrostatic atomization ultrasonic aided low-damage and controllable biologic bone grinding device according to claim 5, wherein the spindle is arranged in an electric spindle housing, a rotor winding is arranged on a circumference of an outer surface of the spindle, and a stator winding corresponding to the rotor winding is arranged in the electric spindle housing;
or the ultrasonic vibration mechanism comprises four piezoelectric ceramic plates, an electrode plate connected with the ultrasonic generator is arranged between two adjacent piezoelectric ceramic plates, and a bottom piezoelectric ceramic plate is connected with a top of the water-catching grinding tool through a horn; spiral grooves are arranged in a surface of the horn;
or a fiber channel is arranged inside the electric spindle housing, and a fiber channel communicating with the fiber channel is arranged inside an endoscope body.

7. The electrostatic atomization ultrasonic aided low-damage and controllable biologic bone grinding device according to claim 6, wherein the spindle is connected with a connecting cylinder through a coupling, the piezoelectric ceramic plates are arranged at a bottom of the connecting cylinder, a sleeve is arranged inside the electric spindle housing, and electric brushes connected with respective electrode plates are arranged in the sleeve.

8. The electrostatic atomization ultrasonic aided low-damage and controllable biologic bone grinding device according to claim 1, wherein the water-catching grinding tool comprises a grinding tool handle, a spherical grinding head base is arranged at a bottom of the grinding tool handle, a plurality of square columnar micro-bulges are arranged on a surface of the grinding head base, and a nano separator film is adhered between the micro-bulges on the surface of the grinding head base.

9. The electrostatic atomization ultrasonic aided low-damage and controllable biologic bone grinding device according to claim 1, wherein an ultrasonic vibration bar is arranged in the medical nanofluid storage cup and connected with the ultrasonic generator.

* * * * *